United States Patent
Braun et al.

(10) Patent No.: US 9,914,710 B2
(45) Date of Patent: Mar. 13, 2018

(54) BICYCLIC ARYLCARBOXYLIC ACID AMIDES AND THEIR USE AS HERBICIDES

(71) Applicant: BAYER CROPSCIENCE AKTIENGESELLSCHAFT, Monheim am Rhein (DE)

(72) Inventors: Ralf Braun, Ramberg (DE); Christian Waldraff, Bad Vilbel (DE); Hansjörg Dietrich, Liederbach am Taunus (DE); Dirk Schmutzler, Hattersheim (DE); Elmar Gatzweiler, Bad Nauheim (DE); Christopher Hugh Rosinger, Hofheim (DE)

(73) Assignee: BAYER CROPSCIENCE AKTIENGESELLSCHAFT, Monheim am Rhein (DE)

( * ) Notice: Subject to any disclaimer, the term of this patent is extended or adjusted under 35 U.S.C. 154(b) by 0 days.

(21) Appl. No.: 15/328,253

(22) PCT Filed: Jul. 24, 2015

(86) PCT No.: PCT/EP2015/066955
§ 371 (c)(1),
(2) Date: Jan. 23, 2017

(87) PCT Pub. No.: WO2016/016107
PCT Pub. Date: Feb. 4, 2016

(65) Prior Publication Data
US 2017/0217909 A1 Aug. 3, 2017

(30) Foreign Application Priority Data
Jul. 28, 2014 (EP) .................................... 14178795

(51) Int. Cl.
| | |
|---|---|
| C07D 257/06 | (2006.01) |
| C07D 249/14 | (2006.01) |
| C07D 271/113 | (2006.01) |
| C07D 271/08 | (2006.01) |
| C07D 405/12 | (2006.01) |
| C07D 409/12 | (2006.01) |
| C07D 409/14 | (2006.01) |
| A01N 43/653 | (2006.01) |
| A01N 43/713 | (2006.01) |
| A01N 43/82 | (2006.01) |

(52) U.S. Cl.
CPC ......... *C07D 257/06* (2013.01); *A01N 43/653* (2013.01); *A01N 43/713* (2013.01); *A01N 43/82* (2013.01); *C07D 249/14* (2013.01); *C07D 271/08* (2013.01); *C07D 271/113* (2013.01); *C07D 405/12* (2013.01); *C07D 409/12* (2013.01); *C07D 409/14* (2013.01)

(58) Field of Classification Search
CPC ................ C07D 257/06; C07D 249/14; C07D 271/113; C07D 271/08; C07D 405/12; C07D 409/12; C07D 409/14
See application file for complete search history.

(56) References Cited

FOREIGN PATENT DOCUMENTS

| WO | 2012/028579 A1 | 3/2012 | |
|---|---|---|---|
| WO | 2012/123409 A1 | 9/2012 | |
| WO | WO 2012123409 A1 * | 9/2012 | ........... C07D 409/12 |
| WO | 2013/064457 A1 | 5/2013 | |
| WO | 2013/092834 A1 | 6/2013 | |
| WO | 2014/086737 A1 | 6/2014 | |

OTHER PUBLICATIONS

International Search Report of International Patent Application No. PCT/EP2015/066955 dated Sep. 24, 2015.

* cited by examiner

*Primary Examiner* — Matthew P Coughlin
(74) *Attorney, Agent, or Firm* — McBee Moore Woodward & Vanik IP, LLC

(57) ABSTRACT

Bicyclic arylcarboxamides of the general formula (I) are described as herbicides.

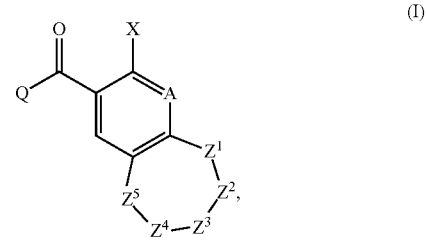

In this formula (I), $Z^1$, $Z^2$, $Z^3$, $Z^4$ and $Z^5$ are a bond, O, S(O)$_n$ or a substituted carbon atom. X is a radical such as hydrogen, organic radicals such as alkyl, and other radicals such as halogen. Q is a substituted heterocycle.

20 Claims, No Drawings

BICYCLIC ARYLCARBOXYLIC ACID AMIDES AND THEIR USE AS HERBICIDES

CROSS-REFERENCE TO RELATED APPLICATIONS

This application is a National Stage entry of International Application No. PCT/EP2015/066955, filed Jul. 24, 2015, which claims priority to European Patent Application No. 14178795.2, filed Jul. 28, 2014.

BACKGROUND

Field of the Invention

The invention relates to the technical field of the herbicides, especially that of the herbicides for selective control of broad-leaved weeds and weed grasses in crops of useful plants.

Description of Related Art

WO 2013/064457 A1 discloses N-(tetrazol-5-yl)- and N-(triazol-5-yl)arylcarboxamides and nicotinamides that bear particular substituents in the 5 position of the aryl ring as herbicides. WO2013092834 A1 discloses N-(tetrazol-5-yl)arylcarboxamides and nicotinamides that are aromatically fused in the 4,5 positions of the aryl ring as herbicides. WO 2014/086737 A1 discloses fused 2-pyridone-3-carboxamides as herbicides. It has now been found that 4,5-bicyclic arylcarboxamides having nonaromatic fusion in the 4,5 positions of the aryl ring are of particularly good suitability as herbicides.

BRIEF SUMMARY OF THE INVENTION

The present invention thus provides bicyclic arylcarboxamides of the formula (I) or salts thereof

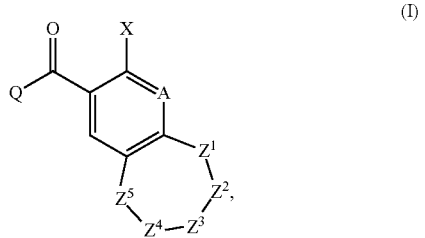

(I)

in which

A is N or CY,

X is nitro, halogen, cyano, formyl, thiocyanato, $(C_1\text{-}C_6)$-alkyl, halo-$(C_1\text{-}C_6)$-alkyl, $(C_2\text{-}C_6)$-alkenyl, halo-$(C_2\text{-}C_6)$-alkenyl, $(C_2\text{-}C_6)$-alkynyl, halo-$(C_3\text{-}C_6)$-alkynyl, $(C_3\text{-}C_6)$-cycloalkyl, halo-$(C_3\text{-}C_6)$-cycloalkyl, $(C_3\text{-}C_6)$-cycloalkyl-$(C_1\text{-}C_6)$-alkyl, halo-$(C_3\text{-}C_6)$-cycloalkyl-$(C_1\text{-}C_6)$-alkyl, $COR^1$, $COOR^1$, $OCOOR^1$, $NR^1COOR^1$, $C(O)N(R^1)_2$, $NR^1C(O)N(R^1)_2$, $OC(O)N(R^1)_2$, $C(O)NR^1OR^1$, $OR^1$, $OCOR^1$, $OSO_2R^2$, $S(O)_nR^2$, $SO_2OR^1$, $SO_2N(R^1)_2$, $NR^1SO_2R^2$, $NR^1COR^1$, $(C_1\text{-}C_6)$-alkyl-$S(O)_nR^2$, $(C_1\text{-}C_6)$-alkyl-$OR^1$, $(C_1\text{-}C_6)$-alkyl-$OCOR^1$, $(C_1\text{-}C_6)$-alkyl-$OSO_2R^2$, $(C_1\text{-}C_6)$-alkyl-$CO_2R^1$, $(C_1\text{-}C_6)$-alkyl-$SO_2OR^1$, $(C_1\text{-}C_6)$-alkyl-$CON(R^1)_2$, $(C_1\text{-}C_6)$-alkyl-$SO_2N(R^1)_2$, $(C_1\text{-}C_6)$-alkyl-$NR^1COR^1$, $(C_1\text{-}C_6)$-alkyl-$NR^1SO_2R^2$, $NR_1R_2$, $P(O)(OR^{11})_2$, $CH_2P(O)(OR^{11})_2$, $(C_1\text{-}C_6)$-alkylheteroaryl, $(C_1\text{-}C_6)$-alkylheterocyclyl, where the latter two radicals are each substituted by s radicals from the group consisting of halogen, $(C_1\text{-}C_6)$-alkyl, halo-$(C_1\text{-}C_6)$-alkyl, $S(O)_n$-$(C_1\text{-}C_6)$-alkyl, $(C_1\text{-}C_6)$-alkoxy and halo-$(C_1\text{-}C_6)$-alkoxy, and where heterocyclyl bears n oxo groups, Y is hydrogen, nitro, halogen, cyano, thiocyanato, $(C_1\text{-}C_6)$-alkyl, halo-$(C_1\text{-}C_6)$-alkyl, $(C_2\text{-}C_6)$-alkenyl, halo-$(C_2\text{-}C_6)$-alkenyl, $(C_2\text{-}C_6)$-alkynyl, halo-$(C_2\text{-}C_6)$-alkynyl, $(C_3\text{-}C_6)$-cycloalkyl, $(C_3\text{-}C_6)$-cycloalkenyl, halo-$(C_3\text{-}C_6)$-cycloalkyl, $(C_3\text{-}C_6)$-cycloalkyl-$(C_1\text{-}C_6)$-alkyl, halo-$(C_3\text{-}C_6)$-cycloalkyl-$(C_1\text{-}C_6)$-alkyl, $COR^1$, $COOR^1$, $OCOOR^1$, $NR^1COOR^1$, $C(O)N(R^1)_2$, $NR^1C(O)N(R^1)_2$, $OC(O)N(R^1)_2$, $CO(NOR^1)R^1$, $C(NOR^1)R^1$, $NR^1SO_2R^2$, $N=S(O)R^2R^2$, $NR^1COR^1$, $OR^1$, $OSO_2R^2$, $S(O)_nR^2$, $S(O)(NR_2)R_2$, $SO2OR1$, $SO_2N(R^1)_2$, $(C_1\text{-}C_6)$-alkyl-$S(O)_nR^2$, $(C_1\text{-}C_6)$-alkyl-$OR^1$, $(C_1\text{-}C_6)$-alkyl-$OCOR^1$, $(C_1\text{-}C_6)$-alkyl-$OSO2R^2$, $(C_1\text{-}C_6)$-alkyl-$CO_2R^1$, $(C_1\text{-}C_6)$-alkyl-CN, $(C_1\text{-}C_6)$-alkyl-$SO_2OR^1$, $(C_1\text{-}C_6)$-alkyl-$CON(R^1)_2$, $(C_1\text{-}C_6)$-alkyl-$SO_2N(R^1)_2$, $(C_1\text{-}C_6)$-alkyl-$NR^1COR^1$, $(C_1\text{-}C_6)$-alkyl-$NR^1SO_2R^2$, $N(R^1)_2$, $P(O)(OR^{11})_2$, $CH_2P(O)(OR^{11})_2$, $(C_1\text{-}C_6)$-alkylphenyl, $(C_1\text{-}C_6)$-alkylheteroaryl, $(C_1\text{-}C_6)$-alkylheterocyclyl, phenyl, heteroaryl or heterocyclyl, where the latter six radicals are each substituted by s radicals from the group consisting of halogen, nitro, cyano, $(C_1\text{-}C_6)$-alkyl, halo-$(C_1\text{-}C_6)$-alkyl, $(C_3\text{-}C_6)$-cycloalkyl, $S(O)_n$-$(C_1\text{-}C_6)$-alkyl, $(C_1\text{-}C_6)$-alkoxy, halo-$(C_1\text{-}C_6)$-alkoxy, $(C_1\text{-}C_6)$-alkoxy-$(C_1\text{-}C_4)$-alkyl and cyanomethyl, and where heterocyclyl bears n oxo groups, $R^1$ is hydrogen, $(C_1\text{-}C_6)$-alkyl, $(C_1\text{-}C_6)$-haloalkyl, $(C_2\text{-}C_6)$-alkenyl, $(C_2\text{-}C_6)$-haloalkenyl, $(C_2\text{-}C_6)$-alkynyl, $(C_2\text{-}C_6)$-haloalkynyl, $(C_3\text{-}C_6)$-cycloalkyl, $(C_3\text{-}C_6)$-cycloalkenyl, $(C_3\text{-}C_6)$-halocycloalkyl, $(C_1\text{-}C_6)$-alkyl-O—$(C_1\text{-}C_6)$-alkyl, $(C_3\text{-}C_6)$-cycloalkyl-$(C_1\text{-}C_6)$-alkyl, phenyl, phenyl-$(C_1\text{-}C_6)$-alkyl, heteroaryl, $(C_1\text{-}C_6)$-alkylheteroaryl, heterocyclyl, $(C_1\text{-}C_6)$-alkylheterocyclyl, $(C_1\text{-}C_6)$-alkyl-O-heteroaryl, $(C_1\text{-}C_6)$-alkyl-O-heterocyclyl, $(C_1\text{-}C_6)$-alkyl-$NR^{12}$-heteroaryl or $(C_1\text{-}C_6)$-alkyl-$NR^{12}$-heterocyclyl, where the latter 21 radicals are each substituted by s radicals from the group consisting of cyano, halogen, nitro, thiocyanato, $OR^{12}$, $S(O)_nR^{13}$, $N(R^{12})_2$, $NR^{12}OR^{12}$, $COR^{12}$, $OCOR^{12}$, $SCOR^{13}$, $NR^{12}COR^{12}$, $NR^{12}SO_2R^{13}$, $CO_2R^{12}$, $COSR^{12}$, $CON(R^{12})_2$, $(C_1\text{-}C_6)$-alkyl and $(C_1\text{-}C_4)$-alkoxy-$(C_2\text{-}C_6)$-alkoxycarbonyl, and where heterocyclyl bears n oxo groups, $R^2$ is $(C_1\text{-}C_6)$-alkyl, $(C_1\text{-}C_6)$-haloalkyl, $(C_2\text{-}C_6)$-alkenyl, $(C_2\text{-}C_6)$-haloalkenyl, $(C_2\text{-}C_6)$-alkynyl, $(C_2\text{-}C_6)$-haloalkynyl, $(C_3\text{-}C_6)$-cycloalkyl, $(C_3\text{-}C_6)$-cycloalkenyl, $(C_3\text{-}C_6)$-halocycloalkyl, $(C_1\text{-}C_6)$-alkyl-O—$(C_1\text{-}C_6)$-alkyl, $(C_3\text{-}C_6)$-cycloalkyl-$(C_1\text{-}C_6)$-alkyl, phenyl, phenyl-$(C_1\text{-}C_6)$-alkyl, heteroaryl, $(C_1\text{-}C_6)$-alkylheteroaryl, heterocyclyl, $(C_1\text{-}C_6)$-alkylheterocyclyl, $(C_1\text{-}C_6)$-alkyl-O-heteroaryl, $(C_1\text{-}C_6)$-alkyl-O-heterocyclyl, $(C_1\text{-}C_6)$-alkyl-$NR^3$-heteroaryl or $(C_1\text{-}C_6)$-alkyl-$NR^3$-heterocyclyl, where the latter 21 radicals are each substituted by s radicals from the group consisting of cyano, halogen, nitro, thiocyanato, $OR^{12}$, $S(O)_nR^{13}$, $N(R^{12})_2$, $NR^{12}OR^{13}$, $COR^{12}$, $OCOR^{12}$, $SCOR^{13}$, $NR^{12}COR^{12}$, $NR^{12}SO_2R^{13}$, $CO_2R^{12}$, $COSR^{13}$, $CON(R^{12})_2$ and $(C_1\text{-}C_4)$-alkoxy-$(C_2\text{-}C_6)$-alkoxycarbonyl, and where heterocyclyl bears n oxo groups, Q is a $Q^1$, $Q^2$, $Q^3$ or $Q^4$ radical,

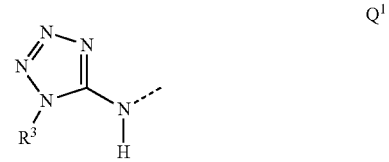

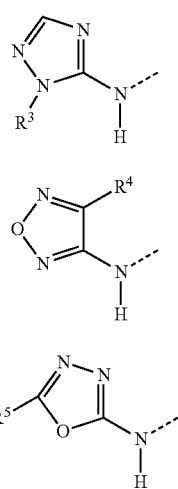

$R^3$ is $(C_1-C_8)$-alkyl, $(C_2-C_8)$-alkenyl, $(C_2-C_8)$-alkynyl, where these radicals are each substituted by s radicals from the group consisting of halogen, cyano, hydroxyl, nitro, $SiR^{11}_3$, $PO(OR^{11})_2$, $S(O)_n-(C_1-C_6)$-alkyl, $(C_1-C_6)$-alkoxy, halo-$(C_1-C_6)$-alkoxy, $COR^{3a}$, $COOR^{3a}$, $OCOR^{3a}$, $NR^{3a}COR^{3a}$, $NR^{3a}SO_2R^{3b}$, $(C_3-C_6)$-cycloalkyl, heteroaryl, heterocyclyl or phenyl, where the latter 4 radicals are each substituted by s radicals from the group consisting of methyl, ethyl, methoxy, trifluoromethyl, cyano and halogen, and where heterocyclyl bears n oxo groups, or $R^3$ is phenyl substituted by s radicals from the group consisting of halogen, nitro, cyano, $(C_1-C_6)$-alkyl, halo-$(C_1-C_6)$-alkyl, $(C_3-C_6)$-cycloalkyl, $S(O)_n-(C_1-C_6)$-alkyl, $(C_1-C_6)$-alkoxy, halo-$(C_1-C_6)$-alkoxy and $(C_1-C_6)$-alkoxy-$(C_1-C_4)$-alkyl, $R^{3a}$ is hydrogen, $(C_1-C_6)$-alkyl, $(C_2-C_6)$-alkenyl, $(C_2-C_6)$-alkynyl, $(C_3-C_6)$-cycloalkyl, $(C_3-C_6)$-cycloalkyl-$(C_1-C_6)$-alkyl or phenyl, $R^{3b}$ is $(C_1-C_6)$-alkyl, $(C_2-C_6)$-alkenyl or $(C_2-C_6)$-alkynyl, $(C_3-C_6)$-cycloalkyl, $(C_3-C_6)$-cycloalkyl-$(C_1-C_6)$-alkyl or phenyl, $R^4$ is hydrogen, $(C_1-C_6)$-alkyl, $(C_3-C_7)$-cycloalkyl, halo-$(C_1-C_6)$-alkyl, $(C_1-C_6)$-alkoxy, halo-$(C_1-C_6)$-alkoxy, $(C_2-C_6)$-alkenyl, $(C_2-C_6)$-alkenyloxy, $(C_2-C_6)$-haloalkenyl, $(C_2-C_6)$-alkynyl, $(C_2-C_6)$-alkynyloxy, $(C_2-C_6)$-haloalkynyl, $(C_1-C_6)$-alkoxy-$(C_1-C_6)$-alkyl, cyano, nitro, methylsulfenyl, methylsulfinyl, methylsulfonyl, acetylamino, benzoylamino, methoxycarbonyl, ethoxycarbonyl, methoxycarbonylmethyl, ethoxycarbonylmethyl, benzoyl, methylcarbonyl, piperidinylcarbonyl, trifluoromethylcarbonyl, halogen, amino, aminocarbonyl, methylaminocarbonyl, dimethylaminocarbonyl, methoxymethyl, or heteroaryl, heterocyclyl or phenyl, each substituted by s radicals from the group consisting of methyl, ethyl, methoxy, trifluoromethyl and halogen, $R^5$ is hydrogen, $(C_1-C_6)$-alkyl, $(C_1-C_6)$-alkoxy-$(C_1-C_6)$-alkyl, $CH_2R_{5a}$, $(C_3-C_7)$-cycloalkyl, halo-$(C_1-C_6)$-alkyl, $(C_2-C_6)$-alkenyl, halo-$(C_2-C_6)$-alkenyl, $(C_2-C_6)$-alkynyl, halo-$(C_2-C_6)$-alkynyl, $(C_1-C_6)$-alkoxy, methylamino, methoxycarbonyl, ethoxycarbonyl, methoxycarbonylmethyl, ethoxycarbonylmethyl, methylcarbonyl, trifluoromethylcarbonyl, dimethylamino, acetylamino, methylsulfenyl, methylsulfinyl, methylsulfonyl, or heteroaryl, heterocyclyl, benzyl or phenyl, each substituted by s radicals from the group consisting of halogen, nitro, cyano, $(C_1-C_6)$-alkyl, halo-$(C_1-C_6)$-alkyl, $(C_3-C_6)$-cycloalkyl, $S(O)_n-(C_1-C_6)$-alkyl, $(C_1-C_6)$-alkoxy, halo-$(C_1-C_6)$-alkoxy and $(C_1-C_6)$-alkoxy-$(C_1-C_4)$-alkyl, $R^{5a}$ is acetoxy, acetamido, N-methylacetamido, benzoyloxy, benzamido, N-methylbenzamido, methoxycarbonyl, ethoxycarbonyl, benzoyl, methylcarbonyl, piperidinylcarbonyl, morpholinylcarbonyl, trifluoromethylcarbonyl, aminocarbonyl, methylaminocarbonyl, dimethylaminocarbonyl, $(C_1-C_6)$-alkoxy or $(C_3-C_6)$-cycloalkyl, or heteroaryl or heterocyclyl, each substituted by s radicals from the group consisting of methyl, ethyl, methoxy, trifluoromethyl and halogen, $Z^1$ is O, $S(O)_n$, $CR^6R^{6'}$ or C=W,
$Z^2$ is O, $NR^1$, $CR^7R^{7'}$ or C=W,
$Z^3$ is a bond, O, $CR^8R^{8'}$ or C=W,
$Z^4$ is a bond, O, $CR^9R^{9'}$ or C=W,
$Z^5$ is O or $CR^{10}R^{10'}$,
with the proviso that at least one of these $Z^1$ to $Z^5$ groups is a substituted carbon atom, and that two of these $Z^1$ to $Z^5$ groups that are directly adjacent are not both oxygen, m is 1, 2, 3 or 4, $R^6$ and $R^{6'}$ are each independently hydrogen, halogen, cyano, hydroxyl, $(C_1-C_4)$-alkyl, $(C_1-C_4)$-haloalkyl, $(C_1-C_4)$-alkoxy, or $R^6$ and $R^{6'}$ form a $(C_2-C_5)$-alkylene group in which n carbon atoms may be by oxygen, $R^7$ and $R^{7'}$ are each independently hydrogen, halogen, cyano, hydroxyl, $(C_1-C_4)$-alkyl, $(C_1-C_4)$-haloalkyl, $(C_1-C_4)$-alkoxy, or $R^7$ and $R^{7'}$ form a $(C_2-C_5)$-alkylene group in which n carbon atoms may be by oxygen, $R^8$ and $R^{8'}$ are each independently hydrogen, halogen, cyano, hydroxyl, $(C_1-C_4)$-alkyl, $(C_1-C_4)$-haloalkyl, $(C_1-C_4)$-alkoxy, or $R^8$ and $R^{8'}$ form a $(C_2-C_5)$-alkylene group in which n carbon atoms may be by oxygen, $R^9$ and $R^{9'}$ are each independently hydrogen, halogen, cyano, hydroxyl, $(C_1-C_4)$-alkyl, $(C_1-C_4)$-haloalkyl, $(C_1-C_4)$-alkoxy, or $R^9$ and $R^{9'}$ form a $(C_2-C_5)$-alkylene group in which n carbon atoms may be by oxygen, $R^{10}$ and $R^{10'}$ are each independently hydrogen, halogen, cyano, hydroxyl, $(C_1-C_4)$-alkyl, $(C_1-C_4)$-haloalkyl, $(C_1-C_4)$-alkoxy, or $R^{10}$ and $R^{10'}$ form a $(C2-C5)$-alkylene group in which n carbon atoms may be by oxygen, W is oxygen, $NOR^1$, $NNR^1R^1$ or $CR^1R^1$, $R^{11}$ is $(C_1-C_4)$-alkyl, $R^{12}$ is hydrogen, $(C_1-C_6)$-alkyl, $(C_2-C_6)$-alkenyl, $(C_2-C_6)$-alkynyl, $(C_3-C_6)$-cycloalkyl, $(C_3-C_6)$-cycloalkyl-$(C_1-C_6)$-alkyl or phenyl, $R^{13}$ is $(C_1-C_6)$-alkyl, $(C_2-C_6)$-alkenyl, $(C_2-C_6)$-alkynyl, $(C_3-C_6)$-cycloalkyl, $(C_3-C_6)$-cycloalkyl-$(C_1-C_6)$-alkyl or phenyl, n is 0, 1 or 2, s is 0, 1, 2, 3, 4 or 5.

In the formula (I) and all the formulae which follow, alkyl radicals having more than two carbon atoms may be straight-chain or branched. Alkyl radicals are, for example, methyl, ethyl, n-propyl or isopropyl, n-, iso-, t- or 2-butyl, pentyls, hexyls such as n-hexyl, isohexyl and 1,3-dimethylbutyl. Analogously, alkenyl is, for example, allyl, 1-methylprop-2-en-1-yl, 2-methylprop-2-en-1-yl, but-2-en-1-yl, but-3-en-1-yl, 1-methylbut-3-en-1-yl and 1-methylbut-2-en-1-yl. Alkynyl is, for example, propargyl, but-2-yn-1-yl, but-3-yn-1-yl, 1-methylbut-3-yn-1-yl. The multiple bond may be in any position in each unsaturated radical. Cycloalkyl is a carbocyclic saturated ring system having three to six carbon atoms, for example cyclopropyl, cyclobutyl, cyclopentyl or cyclohexyl. Analogously, cycloalkenyl is a monocyclic alkenyl group having three to six carbon ring members, for example cyclopropenyl, cyclobutenyl, cyclopentenyl and cyclohexenyl, where the double bond may be in any position.

Halogen is fluorine, chlorine, bromine or iodine.

Heterocyclyl is a saturated, partly saturated or fully unsaturated cyclic radical which contains 3 to 6 ring atoms, of which 1 to 4 are from the group of oxygen, nitrogen and sulfur, and which may additionally be fused by a benzo ring. For example, heterocyclyl is piperidinyl, pyrrolidinyl, tetrahydrofuranyl, dihydrofuranyl and oxetanyl.

Heteroaryl is an aromatic cyclic radical which contains 3 to 6 ring atoms, of which 1 to 4 are from the group of oxygen, nitrogen and sulfur, and which may additionally be fused by a benzo ring. For example, heteroaryl is benzimidazol-2-yl, furanyl, imidazolyl, isoxazolyl, isothiazolyl, oxazolyl, pyrazinyl, pyrimidinyl, pyridazinyl, pyridinyl, benzisoxazolyl, thiazolyl, pyrrolyl, pyrazolyl, thiophenyl, 1,2,3-oxadiazolyl, 1,2,4-oxadiazolyl, 1,2,5-oxadiazolyl, 1,3,4-oxadiazolyl, 1,2,4-triazolyl, 1,2,3-triazolyl, 1,2,5-triazolyl, 1,3,4-triazolyl, 1,2,4-triazolyl, 1,2,4-thiadiazolyl, 1,3,4-thiadiazolyl, 1,2,3-thiadiazolyl, 1,2,5-thiadiazolyl, 2H-1,2,3,4-tetrazolyl, 1H-1,2,3,4-tetrazolyl, 1,2,3,4-oxatriazolyl, 1,2,3,5-oxatriazolyl, 1,2,3,4-thiatriazolyl and 1,2,3,5-thiatriazolyl.

If a group is polysubstituted by radicals, this should be understood to mean that this group is substituted by one or more identical or different radicals selected from the radicals mentioned. The same applies to the formation of ring systems by different atoms and elements. At the same time, the scope of the claims shall exclude those compounds known by the person skilled in the art to be chemically unstable under standard conditions.

Depending on the nature of the substituents and the manner in which they are attached, the compounds of the general formula (I) may be present as stereoisomers. If, for example, one or more asymmetric carbon atoms are present, enantiomers and diastereomers may occur. Stereoisomers likewise occur when n is 1 (sulfoxides). Stereoisomers can be obtained from the mixtures obtained in the preparation by customary separation methods, for example by chromatographic separation processes. It is likewise possible to selectively prepare stereoisomers by using stereoselective reactions with use of optically active starting materials and/or auxiliaries. The invention also relates to all the stereoisomers and mixtures thereof that are encompassed by the general formula (I) but are not defined specifically. Owing to the oxime ether structure, the compounds of the invention may also occur as geometric isomers (E/Z isomers). The invention also relates to all E/Z isomers and mixtures thereof which are encompassed by the general formula (I) but not defined specifically.

The compounds of the formula (I) are capable of forming salts. Salts can be formed by the action of a base on those compounds of the formula (I) which bear an acidic hydrogen atom, for example in the case that $R^1$ contains a COOH group or a sulfonamide group —$NHSO_2$—. Examples of suitable bases are organic amines such as trialkylamines, morpholine, piperidine or pyridine, and the hydroxides, carbonates and hydrogencarbonates of ammonium, alkali metals or alkaline earth metals, especially sodium hydroxide, potassium hydroxide, sodium carbonate, potassium carbonate, sodium hydrogencarbonate and potassium hydrogencarbonate. These salts are compounds in which the acidic hydrogen is replaced by an agriculturally suitable cation, for example metal salts, especially alkali metal salts or alkaline earth metal salts, especially sodium and potassium salts, or else ammonium salts, salts with organic amines or quaternary ammonium salts, for example with cations of the formula [NRR'R''R''']$^+$ in which R to R''' are each independently an organic radical, especially alkyl, aryl, aralkyl or alkylaryl. Also suitable are alkylsulfonium and alkylsulfoxonium salts, such as ($C_1$-$C_4$)-trialkylsulfonium and ($C_1$-$C_4$)-trialkylsulfoxonium salts.

DETAILED DESCRIPTION OF A PREFERRED EMBODIMENT

The compounds of the formula (I) can form salts by addition of a suitable inorganic or organic acid, for example mineral acids, for example HCl, HBr, $H_2SO_4$, $H_3PO_4$ or $HNO_3$, or organic acids, for example carboxylic acids such as formic acid, acetic acid, propionic acid, oxalic acid, lactic acid or salicylic acid or sulfonic acids, for example p-toluenesulfonic acid, onto a basic group, for example amino, alkylamino, dialkylamino, piperidino, morpholino or pyridino. In such a case, these salts will comprise the conjugate base of the acid as the anion.

Preference is given to compounds of the general formula (I) in which

A is N or CY,

X is nitro, halogen, cyano, thiocyanato, ($C_1$-$C_6$)-alkyl, halo-($C_1$-$C_6$)-alkyl, ($C_2$-$C_6$)-alkenyl, halo-($C_2$-$C_6$)-alkenyl, ($C_2$-$C_6$)-alkynyl, halo-($C_3$-$C_6$)-alkynyl, ($C_3$-$C_6$)-cycloalkyl, halo-($C_3$-$C_6$)-cycloalkyl, ($C_1$-$C_6$)-alkyl-O—($C_1$-$C_6$)-alkyl, ($C_3$-$C_6$)-cycloalkyl-($C_1$-$C_6$)-alkyl, halo-($C_3$-$C_6$)-cycloalkyl-($C_1$-$C_6$)-alkyl, $COR^1$, $OR^1$, $OCOR^1$, $OSO_2R^2$, $S(O)_nR^2$, $SO_2OR^1$, $SO_2N(R^1)_2$, $NR^1SO_2R^2$, $NR^1COR^1$, ($C_1$-$C_6$)-alkyl-S(O)$_n$$R^2$, ($C_1$-$C_6$)-alkyl-$OR^1$, ($C_1$-$C_6$)-alkyl-$OCOR^1$, ($C_1$-$C_6$)-alkyl-$OSO_2R^2$, ($C_1$-$C_6$)-alkyl-$CO_2R^1$, ($C_1$-$C_6$)-alkyl-$SO_2OR^1$, ($C_1$-$C_6$)-alkyl-$CON(R^1)_2$, ($C_1$-$C_6$)-alkyl-$SO_2N(R^1)_2$, ($C_1$-$C_6$)-alkyl-$NR^1COR^1$ or ($C_1$-$C_6$)-alkyl-$NR^1SO_2R^2$, ($C_1$-$C_6$)-alkylheteroaryl, ($C_1$-$C_6$)-alkylheterocyclyl, where the latter two radicals may each be substituted by s radicals from the group consisting of halogen, ($C_1$-$C_6$)-alkyl, halo-($C_1$-$C_6$)-alkyl, S(O)$_n$—($C_1$-$C_6$)-alkyl, ($C_1$-$C_6$)-alkoxy and halo-($C_1$-$C_6$)-alkoxy, and where heterocyclyl bears n oxo groups, Y is hydrogen, nitro, halogen, cyano, thiocyanato, ($C_1$-$C_6$)-alkyl, halo-($C_1$-$C_6$)-alkyl, ($C_2$-$C_6$)-alkenyl, halo-($C_2$-$C_6$)-alkenyl, ($C_2$-$C_6$)-alkynyl, halo-($C_3$-$C_6$)-alkynyl, ($C_3$-$C_6$)-cycloalkyl, ($C_3$-$C_6$)-cycloalkenyl, halo-($C_3$-$C_6$)-cycloalkyl, ($C_3$-$C_6$)-cycloalkyl-($C_1$-$C_6$)-alkyl, halo-($C_3$-$C_6$)-cycloalkyl-($C_1$-$C_6$)-alkyl, $COR^1$, $OR^1$, $COOR^1$, $OSO_2R^2$, $S(O)_nR^2$, $SO_2OR^1$, $SO_2N(R^1)_2$, $N(R^1)_2$, $NR^1SO_2R^2$, $NR^1COR^1$, ($C_1$-$C_6$)-alkyl-S(O)$_n$$R^2$, ($C_1$-$C_6$)-alkyl-$OR^1$, ($C_1$-$C_6$)-alkyl-$OCOR^1$, ($C_1$-$C_6$)-alkyl-$OSO_2R^2$, ($C_1$-$C_6$)-alkyl-$CO_2R^1$, ($C_1$-$C_6$)-alkyl-$SO_2OR^1$, ($C_1$-$C_6$)-alkyl-$CON(R^1)_2$, ($C_1$-$C_6$)-alkyl-$SO_2N(R^1)_2$, ($C_1$-$C_6$)-alkyl-$NR^1COR^1$, ($C_1$-$C_6$)-alkyl-$NR^1SO_2R^2$, ($C_1$-$C_6$)-alkylphenyl, ($C_1$-$C_6$)-alkylheteroaryl, ($C_1$-$C_6$)-alkylheterocyclyl, phenyl, heteroaryl or heterocyclyl, where the latter six radicals are each substituted by s radicals from the group consisting halogen, nitro, cyano, ($C_1$-$C_6$)-alkyl, halo-($C_1$-$C_6$)-alkyl, ($C_3$-$C_6$)-cycloalkyl, S(O)$_n$—($C_1$-$C_6$)-alkyl, ($C_1$-$C_6$)-alkoxy, halo-($C_1$-$C_6$)-alkoxy, ($C_1$-$C_6$)-alkoxy-($C_1$-$C_4$)-alkyl and cyanomethyl, and where heterocyclyl bears n oxo groups, $R^1$ is hydrogen, $(C_1\text{-}C_6)$-alkyl, $(C_2\text{-}C_6)$-alkenyl, $(C_2\text{-}C_6)$-alkynyl, $(C_3\text{-}C_6)$-cycloalkyl, $(C_3\text{-}C_6)$-cycloalkyl-$(C_1\text{-}C_6)$-alkyl, $(C_1\text{-}C_6)$-alkyl-O—$(C_1\text{-}C_6)$-alkyl, phenyl, phenyl-$(C_1\text{-}C_6)$-alkyl, heteroaryl, $(C_1\text{-}C_6)$-alkylheteroaryl, heterocyclyl, $(C_1\text{-}C_6)$-alkylheterocyclyl, $(C_1\text{-}C_6)$-alkyl-O-heteroaryl, $(C_1\text{-}C_6)$-alkyl-O-heterocyclyl, $(C_1\text{-}C_6)$-alkyl-$NR^{12}$-heteroaryl or $(C_1\text{-}C_6)$-alkyl-$NR^{12}$-heterocyclyl, where the latter sixteen radicals are each substituted by s radicals from the group consisting of cyano, halogen, nitro, $OR^{12}$, $S(O)_nR^{13}$, $N(R^{12})_2$, $NR^{12}OR^{12}$, $COR^{12}$, $OCOR^{12}$, $NR^{12}COR^{12}$, $NR^{12}SO_2R^{13}$, $CO_2R^{12}$, $CON(R^{12})_2$ and $(C_1\text{-}C_4)$-alkoxy-$(C_2\text{-}C_6)$-alkoxycarbonyl, and where heterocyclyl bears n oxo groups, $R^2$ is $(C_1\text{-}C_6)$-alkyl, $(C_2\text{-}C_6)$-alkenyl, $(C_2\text{-}C_6)$-alkynyl, $(C_3\text{-}C_6)$-cycloalkyl, $(C_3\text{-}C_6)$-cycloalkyl-$(C_1\text{-}C_6)$-alkyl, $(C_1\text{-}C_6)$-alkyl-O—$(C_1\text{-}C_6)$-alkyl, phenyl, phenyl-$(C_1\text{-}C_6)$-alkyl, heteroaryl, $(C_1\text{-}C_6)$-alkylheteroaryl, heterocyclyl, $(C_1\text{-}C_6)$-alkylheterocyclyl, $(C_1\text{-}C_6)$-alkyl-O-heteroaryl, $(C_1\text{-}C_6)$-alkyl-O-heterocyclyl, $(C_1\text{-}C_6)$-alkyl-$NR^{12}$-heteroaryl or $(C_1\text{-}C_6)$-alkyl-$NR^{12}$-heterocyclyl, where these latter sixteen radicals are each substituted by s radicals from the group consisting of cyano, halogen, nitro, $OR^{12}$, $S(O)_nR^{13}$, $N(R^{12})_2$, $NR^{12}OR^{12}$, $NR^{12}SO_2R^{13}$, $COR^{12}$, $OCOR^{12}$, $NR^{12}COR^{12}$, $CO_2R^{12}$, $CON(R^{12})_2$ and $(C_1\text{-}C_4)$-alkoxy-$(C_2\text{-}C_6)$-alkoxycarbonyl, and where heterocyclyl bears n oxo groups, Q is a $Q^1$, $Q^2$, $Q^3$ or $Q^4$ radical,

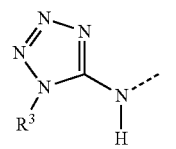

$Q^1$

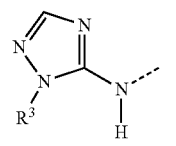

$Q^2$

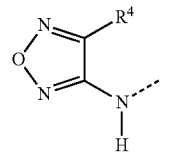

$Q^3$

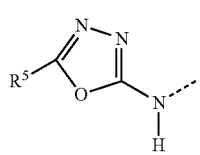

$Q^4$ $R^3$ is $(C_1\text{-}C_8)$-alkyl, $(C_2\text{-}C_8)$-alkenyl, $(C_2\text{-}C_8)$-alkynyl, where these radicals are each substituted by s radicals from the group consisting of halogen, cyano, nitro, $S(O)_n$—$(C_1\text{-}C_6)$-alkyl, $(C_1\text{-}C_6)$-alkoxy, halo-$(C_1\text{-}C_6)$-alkoxy, $(C_3\text{-}C_6)$-cycloalkyl, heteroaryl, heterocyclyl or phenyl, where the latter 4 radicals are each substituted by p radicals from the group consisting of methyl, ethyl, methoxy, trifluoromethyl, cyano and halogen, and where heterocyclyl bears n oxo groups, or $R^3$ is phenyl substituted in each case by p radicals from the group consisting of halogen, nitro, cyano, $(C_1\text{-}C_6)$-alkyl, halo-$(C_1\text{-}C_6)$-alkyl, $(C_3\text{-}C_6)$-cycloalkyl, $S(O)_n$—$(C_1\text{-}C_6)$-alkyl, $(C_1\text{-}C_6)$-alkoxy, halo-$(C_1\text{-}C_6)$-alkoxy and $(C_1\text{-}C_6)$-alkoxy-$(C_1\text{-}C_4)$-alkyl, $R^4$ is $(C_1\text{-}C_6)$-alkyl, $(C_3\text{-}C_7)$-cycloalkyl, halo-$(C_1\text{-}C_6)$-alkyl, $(C_1\text{-}C_6)$-alkoxy, halo-$(C_1\text{-}C_6)$-alkoxy, cyano, nitro, methylsulfenyl, methylsulfinyl, methylsulfonyl, $(C_1\text{-}C_4)$-alkylcarbonylamino, benzoylamino, methoxycarbonyl, ethoxycarbonyl, benzoyl, phenoxy, methylcarbonyl, piperidinylcarbonyl, trifluoromethylcarbonyl, halogen, amino, aminocarbonyl, methylaminocarbonyl, dimethylaminocarbonyl, methoxymethyl, 1,2,4-triazol-1-yl, pyrazol-1-yl, 2-thiophenyl, 2-pyridinyl, 3-pyridinyl, 4-pyridinyl, 1,2,4-oxadiazol-3-yl, benzoxazol-2-yl, 1-ethylbenzimidazol-2-yl, piperidin-1-yl, or phenyl substituted in each case by p radicals from the group consisting of methyl, ethyl, methoxy, trifluoromethyl and halogen, $R^5$ is hydrogen, $(C_1\text{-}C_6)$-alkyl, $(C_3\text{-}C_7)$-cycloalkyl, halo-$(C_1\text{-}C_6)$-alkyl, $(C_3\text{-}C_7)$-cycloalkylmethyl, methoxycarbonylmethyl, ethoxycarbonylmethyl, acetylmethyl, methoxymethyl, methoxyethyl, benzyl, pyrazin-2-yl, furan-2-yl, tetrahydrofuran-2-yl, morpholine or dimethylamino, or phenyl substituted by p radicals from the group consisting of methyl, methoxy, trifluoromethyl and halogen, $Z^1$ is O, $S(O)_n$, $CR^6R^{6'}$ or C=W, $Z^2$ is O, NMe or $CH_2$, $Z^3$ is a bond, O or $CH_2$, $Z^4$ is a bond, $Z^5$ is O or $CH_2$, with the proviso that at least one of these $Z^1$ to $Z^5$ groups is a substituted carbon atom, and that two of these $Z^1$ to $Z^5$ groups that are directly adjacent are not both oxygen, m is 1, 2, 3 or 4, $R^6$ and $R^{6'}$ are each independently hydrogen, halogen, cyano, hydroxyl, $(C_1\text{-}C_4)$-alkyl, $(C_1\text{-}C_4)$-alkoxy, or $R^6$ and $R^{6'}$ form a $(C_2\text{-}C_5)$-alkylene group in which n carbon atoms may be by oxygen, W is oxygen, $NO(C_1\text{-}C_6)$-alkyl, $CH_2$, CHMe, $CMe_2$ $R^{12}$ is hydrogen or $(C_1\text{-}C_6)$-alkyl, $R^{13}$ is $(C_1\text{-}C_6)$-alkyl, n is 0, 1 or 2, s is 0, 1, 2, 3, 4 or 5.

Particular preference is given to compounds of the general formula (I) in which

A is N or CY,

X is nitro, halogen, cyano, $(C_1\text{-}C_6)$-alkyl, halo-$(C_1\text{-}C_6)$-alkyl, $(C_3\text{-}C_6)$-cycloalkyl, $OR^1$, $S(O)_nR^2$, $(C_1\text{-}C_6)$-alkyl-$S(O)_nR^2$, $(C_1\text{-}C_6)$-alkyl-$OR^1$, $(C_1\text{-}C_6)$-alkyl-$CON(R^1)_2$, $(C_1\text{-}C_6)$-alkyl-$SO_2N(R^1)_2$, $(C_1\text{-}C_6)$-alkyl-$NR^1COR^1$, $(C_1\text{-}C_6)$-alkyl-$NR^1SO_2R^2$, $(C_1\text{-}C_6)$-alkylheteroaryl, $(C_1\text{-}C_6)$-alkylheterocyclyl, where the latter two radicals are each substituted by s halogen, $(C_1\text{-}C_6)$-alkyl, halo-$(C_1\text{-}C_6)$-alkyl, $S(O)_n$—$(C_1\text{-}C_6)$-alkyl, $(C_1\text{-}C_6)$-alkoxy and halo-$(C_1\text{-}C_6)$-alkoxy radicals, and where heterocyclyl bears n oxo groups, Y is hydrogen, nitro, halogen, cyano, $(C_1\text{-}C_6)$-alkyl, $(C_1\text{-}C_6)$-haloalkyl, $OR^1$, $S(O)_nR^2$, $SO_2N(R^1)_2$, $N(R^1)_2$, $NR^1SO_2R^2$, $NR^1COR^1$, $(C_1\text{-}C_6)$-alkyl-$S(O)_nR^2$, $(C_1\text{-}C_6)$-alkyl-$OR^1$, $(C_1\text{-}C_6)$-alkyl-$CON(R^1)_2$, $(C_1\text{-}C_6)$-alkyl-$SO_2N(R^1)_2$, $(C_1\text{-}C_6)$-alkyl-$NR^1COR^1$, $(C_1\text{-}C_6)$-alkyl-$NR^1SO_2R^2$, $(C_1\text{-}C_6)$-alkylphenyl, $(C_1\text{-}C_6)$-alkylheteroaryl, $(C_1\text{-}C_6)$-alkylheterocyclyl, phenyl, heteroaryl or heterocyclyl, where the latter six radicals are each substituted by s radicals from the group consisting halogen, nitro, cyano, $(C_1\text{-}C_6)$-alkyl, halo-$(C_1\text{-}C_6)$-alkyl, $(C_3\text{-}C_6)$-cycloalkyl, $S(O)_n$—$(C_1\text{-}C_6)$-alkyl, $(C_1\text{-}C_6)$- alkoxy, halo-$(C_1-C_6)$-alkoxy, $(C_1-C_6)$-alkoxy-$(C_1-C_4)$-alkyl and cyanomethyl, and where heterocyclyl bears n oxo groups, $R^1$ is hydrogen, $(C_1-C_6)$-alkyl, $(C_2-C_6)$-alkenyl, $(C_2-C_6)$-alkynyl, $(C_3-C_6)$-cycloalkyl, $(C_3-C_6)$-cycloalkyl-$(C_1-C_6)$-alkyl, $(C_1-C_6)$-alkyl-O—$(C_1-C_6)$-alkyl, phenyl, phenyl-$(C_1-C_6)$-alkyl, heteroaryl, $(C_1-C_6)$-alkylheteroaryl, heterocyclyl, $(C_1-C_6)$-alkylheterocyclyl, $(C_1-C_6)$-alkyl-O-heteroaryl, $(C_1-C_6)$-alkyl-O-heterocyclyl, $(C_1-C_6)$-alkyl-$NR^{12}$-heteroaryl or $(C_1-C_6)$-alkyl-$NR^3$-heterocyclyl, where the latter sixteen radicals are each substituted by s radicals from the group consisting of cyano, halogen, nitro, $OR^{12}$, $S(O)_nR^{13}$, $N(R^{12})_2$, $NR^{12}OR^{12}$, $COR^{12}$, $OCOR^{12}$, $NR^{12}COR^{12}$, $NR^{12}SO_2R^{13}$, $CO_2R^{12}$, $CON(R^{12})_2$ and $(C_1-C_4)$-alkoxy-$(C_2-C_6)$-alkoxycarbonyl, and where heterocyclyl bears n oxo groups, $R^2$ is $(C_1-C_6)$-alkyl, $(C_3-C_6)$-cycloalkyl or $(C_3-C_6)$-cycloalkyl-$(C_1-C_6)$-alkyl, each substituted by s radicals from the group consisting of halogen and $OR^{12}$, Q is a $Q^1$, $Q^2$, $Q^3$ or $Q^4$ radical,

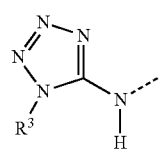

$Q^1$

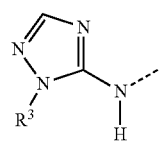

$Q^2$

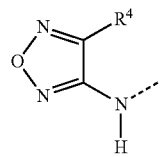

$Q^3$

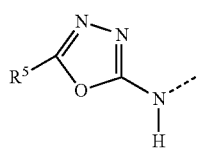

$Q^4$ $R^3$ is $(C_1-C_8)$-alkyl, $(C_2-C_8)$-alkenyl or $(C_2-C_8)$-alkynyl, each substituted by s radicals from the group consisting of halogen, cyano, nitro, $S(O)_n$—$(C_1-C_6)$-alkyl, $(C_1-C_6)$-alkoxy and halo-$(C_1-C_6)$-alkoxy, $R^4$ is $(C_1-C_6)$-alkyl, $(C_3-C_7)$-cycloalkyl, halo-$(C_1-C_6)$-alkyl, $(C_1-C_6)$-alkoxy, halo-$(C_1-C_6)$-alkoxy, cyano, nitro, methylsulfenyl, methylsulfinyl, methylsulfonyl, $(C_1-C_4)$-alkylcarbonylamino, benzoylamino, methoxycarbonyl, ethoxycarbonyl, benzoyl, phenoxy, methylcarbonyl, piperidinylcarbonyl, trifluoromethylcarbonyl, halogen, amino, aminocarbonyl, methylaminocarbonyl, dimethylaminocarbonyl, methoxymethyl, 1,2,4-triazole-1H, 1-pyrazole-1H, 2-thiophenyl, 2-pyridinyl, 3-pyridinyl, 4-pyridinyl, 1,2,4-oxadiazol-3-yl, benzoxazol-2-yl, 1-ethylbenzimidazol-2-yl, piperidin-1-yl, or phenyl substituted in each case by s radicals from the group consisting of methyl, ethyl, methoxy, trifluoromethyl and halogen, $R^5$ is hydrogen, $(C_1-C_6)$-alkyl, $(C_3-C_7)$-cycloalkyl, halo-$(C_1-C_6)$-alkyl, $(C_3-C_7)$-cycloalkylmethyl, methoxycarbonylmethyl, ethoxycarbonylmethyl, acetylmethyl, methoxymethyl, methoxyethyl, benzyl, pyrazin-2-yl, furan-2-yl, tetrahydrofuran-2-yl, morpholine or dimethylamino, or phenyl substituted by p radicals from the group consisting of methyl, methoxy, trifluoromethyl and halogen, $Z^1$ is O, $SO_2$, $CR^6R^{6'}$ or C=W, $Z^2$ is O or $CH_2$, $Z^3$ is a bond, O or $CH_2$, $Z^4$ is a bond, $Z^5$ is O or $CH_2$, with the proviso that at least one of these $Z^1$ to $Z^5$ groups is a substituted carbon atom, and that two of these $Z^1$ to $Z^5$ groups that are directly adjacent are not both oxygen, m is 1, 2, 3 or 4, $R^6$ and $R^{6'}$ are each independently hydrogen, fluorine, hydroxyl, $(C_1-C_4)$-alkyl, $(C_1-C_4)$-alkoxy, or $R^6$ and $R^{6'}$ form a $(C_2-C_5)$-alkylene group in which n carbon atoms may be by oxygen, W is oxygen or $NO(C_1-C_6)$-alkyl, $R^{12}$ is hydrogen or $(C_1-C_6)$-alkyl, $R^{13}$ is $(C_1-C_6)$-alkyl, n is 0, 1 or 2, s is 0, 1, 2, 3, 4 or 5.

In all the formulae specified hereinafter, the substituents and symbols have the same meaning as described in formula (I), unless defined differently.

Compounds of the invention in which Q is $Q^1$ or $Q^2$ can be prepared, for example, according to scheme 1 by the method specified in WO 2012/028579 A1. Compounds of the invention in which Q is $Q^3$ can be prepared, for example, according to scheme 1 by the method specified in WO 2012/123416 A1. Compounds of the invention in which Q is $Q^4$ can be prepared, for example, according to scheme 1 by the method specified in WO 2012/126932 A1. The corresponding ester precursors can be prepared, for example, according to the following scheme:

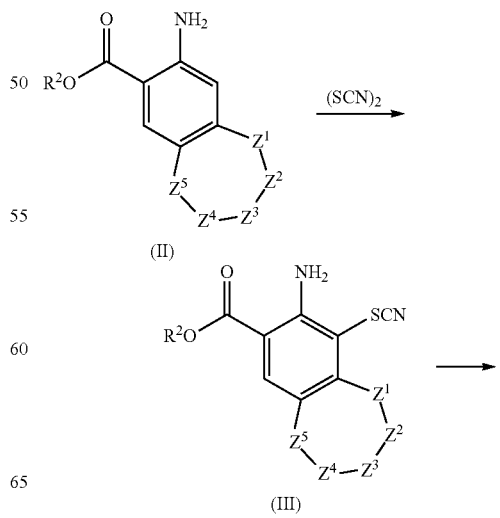

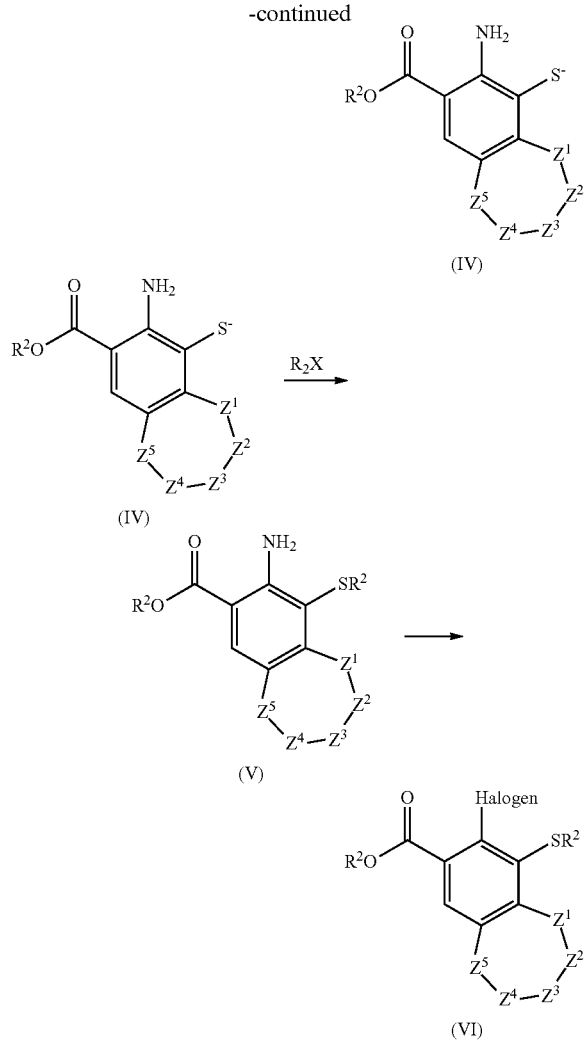

It is possible, for example, to convert the corresponding anthranilic ester (II) with thiocyanogen, prepared from a thiocyanate salt and an oxidizing agent, for example bromine, to the corresponding thiocyanate (III). The latter can subsequently be converted to the corresponding thiol, or thiolate (IV), for example by reaction with sodium sulfide. Reaction with an alkylating agent affords the desired thioether (V). These reaction steps proceeding from (II) to (V) can advantageously be executed successively in one reaction vessel without isolating the intermediates (III) and (IV). The conversion from the aniline (V) to the halide (VI) can be effected by diazotizing halogenation in an aqueous or anhydrous medium.

It may be appropriate to alter the sequence of the reaction steps. For instance, benzoic acids bearing a sulfoxide cannot be converted directly to their acid chlorides. One option here is first to prepare the amide at the thioether stage, and then to oxidize the thioether to the sulfoxide.

Collections of compounds of the formula (I) and/or salts thereof which can be synthesized by the abovementioned reactions can also be prepared in a parallelized manner, in which case this may be accomplished in a manual, partly automated or fully automated manner. It is possible, for example, to automate the conduct of the reaction, the workup or the purification of the products and/or intermediates. Overall, this is understood to mean a procedure as described, for example, by D. Tiebes in Combinatorial Chemistry—Synthesis, Analysis, Screening (editor Günther Jung), Wiley, 1999, on pages 1 to 34.

For the parallelized conduct of the reaction and workup, it is possible to use a number of commercially available instruments, for example Calypso reaction blocks from Barnstead International, Dubuque, Iowa 52004-0797, USA or reaction stations from Radleys, Shirehill, Saffron Walden, Essex, CB11 3AZ, England, or MultiPROBE Automated Workstations from PerkinElmer, Waltham, Mass. 02451, USA. For the parallelized purification of compounds of the general formula (I) and salts thereof or of intermediates which occur in the course of preparation, available apparatuses include chromatography apparatuses, for example from ISCO, Inc., 4700 Superior Street, Lincoln, Nebr. 68504, USA.

The apparatuses detailed lead to a modular procedure in which the individual working steps are automated, but manual operations have to be carried out between the working steps. This can be circumvented by using partly or fully integrated automation systems in which the respective automation modules are operated, for example, by robots. Automation systems of this type can be obtained, for example, from Caliper, Hopkinton, Mass. 01748, USA.

The implementation of single or multiple synthesis steps can be supported by the use of polymer-supported reagents/ scavenger resins. The specialist literature describes a series of experimental protocols, for example in ChemFiles, Vol. 4, No. 1, Polymer-Supported Scavengers and Reagents for Solution-Phase Synthesis (Sigma-Aldrich).

Aside from the methods described here, compounds of the general formula (I) and salts thereof can be prepared completely or partially by solid-phase-supported methods. For this purpose, individual intermediates or all intermediates in the synthesis or a synthesis adapted for the corresponding procedure are bound to a synthesis resin. Solid-phase-supported synthesis methods are described adequately in the technical literature, for example Barry A. Bunin in "The Combinatorial Index", Academic Press, 1998 and Combinatorial Chemistry—Synthesis, Analysis, Screening (editor: Günther Jung), Wiley, 1999. The use of solid-phase-supported synthesis methods permits a number of protocols, which are known from the literature and which for their part may be performed manually or in an automated manner. The reactions can be performed, for example, by means of IRORI technology in microreactors from Nexus Biosystems, 12140 Community Road, Poway, Calif. 92064, USA.

Both in the solid and in the liquid phase, the implementation of individual or several synthesis steps may be supported by the use of microwave technology. The specialist literature describes a series of experimental protocols, for example in Microwaves in Organic and Medicinal Chemistry (editor: C. O. Kappe and A. Stadler), Wiley, 2005.

The preparation by the processes described here gives compounds of the formula (I) and salts thereof in the form of substance collections, which are called libraries. The present invention also provides libraries comprising at least two compounds of the formula (I) and salts thereof.

The compounds of the invention have excellent herbicidal efficacy against a broad spectrum of economically important mono- and dicotyledonous annual harmful plants. The active ingredients also act efficiently on perennial weeds which produce shoots from rhizomes, root stocks and other perennial organs and which are difficult to control.

The present invention therefore also provides a method for controlling unwanted plants or for regulating the growth of plants, preferably in plant crops, in which one or more compound(s) of the invention is/are applied to the plants (for example harmful plants such as monocotyledonous or dicotyledonous weeds or unwanted crop plants), the seed (for example grains, seeds or vegetative propagules such as tubers or shoot parts with buds) or the area on which the plants grow (for example the area under cultivation). The compounds of the invention can be deployed, for example, prior to sowing (if appropriate also by incorporation into the soil), prior to emergence or after emergence. Specific examples of some representatives of the monocotyledonous and dicotyledonous weed flora which can be controlled by the compounds of the invention are as follows, though there is no intention to restrict the enumeration to particular species.

Monocotyledonous harmful plants of the genera: *Aegilops, Agropyron, Agrostis, Alopecurus, Apera, Avena, Brachiaria, Bromus, Cenchrus, Commelina, Cynodon, Cyperus, Dactyloctenium, Digitaria, Echinochloa, Eleocharis, Eleusine, Eragrostis, Eriochloa, Festuca, Fimbristylis, Heteranthera, Imperata, Ischaemum, Leptochloa, Lolium, Monochoria, Panicum, Paspalum, Phalaris, Phleum, Poa, Rottboellia, Sagittaria, Scirpus, Setaria* and *Sorghum.*

Dicotyledonous weeds of the genera: *Abutilon, Amaranthus, Ambrosia, Anoda, Anthemis, Aphanes, Artemisia, Atriplex, Bellis, Bidens, Capsella, Carduus, Cassia, Centaurea, Chenopodium, Cirsium, Convolvulus, Datura, Desmodium, Emex, Erysimum, Euphorbia, Galeopsis, Galinsoga, Galium, Hibiscus, Ipomoea, Kochia, Lamium, Lepidium, Lindernia, Matricaria, Mentha, Mercurialis, Mullugo, Myosotis, Papaver, Pharbitis, Plantago, Polygonum, Portulaca, Ranunculus, Raphanus, Rorippa, Rotala, Rumex, Salsola, Senecio, Sesbania, Sida, Sinapis, Solanum, Sonchus, Sphenoclea, Stellaria, Taraxacum, Thlaspi, Trifolium, Urtica, Veronica, Viola* and *Xanthium.*

If the compounds of the invention are applied to the soil surface before germination, either the emergence of the weed seedlings is prevented completely or the weeds grow until they have reached the cotyledon stage, but then they stop growing and ultimately die completely after three to four weeks have passed.

If the active ingredients are applied post-emergence to the green parts of the plants, growth stops after the treatment, and the harmful plants remain at the growth stage at the time of application, or they die completely after a certain time, such that competition by the weeds, which is harmful to the crop plants, is thus eliminated very early and in a lasting manner.

Although the compounds of the invention have outstanding herbicidal activity against monocotyledonous and dicotyledonous weeds, crop plants of economically important crops, for example dicotyledonous crops of the genera *Arachis, Beta, Brassica, Cucumis, Cucurbita, Helianthus, Daucus, Glycine, Gossypium, Ipomoea, Lactuca, Linum, Lycopersicon, Miscanthus, Nicotiana, Phaseolus, Pisum, Solanum, Vicia,* or monocotyledonous crops of the genera *Allium, Ananas, Asparagus, Avena, Hordeum, Oryza, Panicum, Saccharum, Secale, Sorghum, Triticale, Triticum, Zea,* in particular *Zea* and *Triticum,* will be damaged to a negligible extent only, if at all, depending on the structure of the particular compound of the invention and its application rate. For these reasons, the present compounds are very suitable for selective control of unwanted plant growth in plant crops such as agriculturally useful plants or ornamental plants.

In addition, the compounds of the invention, depending on their particular chemical structure and the application rate deployed, have outstanding growth-regulating properties in crop plants. They intervene in the plants' own metabolism with regulatory effect, and can thus be used for the controlled influencing of plant constituents and to facilitate harvesting, for example by triggering desiccation and stunted growth. In addition, they are also suitable for general control and inhibition of unwanted vegetative growth without killing the plants. Inhibition of vegetative growth plays a major role for many mono- and dicotyledonous crops since, for example, this can reduce or completely prevent lodging.

By virtue of their herbicidal and plant growth regulatory properties, the active ingredients can also be used to control harmful plants in crops of genetically modified plants or plants modified by conventional mutagenesis. In general, the transgenic plants are characterized by particular advantageous properties, for example by resistances to certain pesticides, in particular certain herbicides, resistances to plant diseases or pathogens of plant diseases, such as certain insects or microorganisms such as fungi, bacteria or viruses. Other specific characteristics relate, for example, to the harvested material with regard to quantity, quality, storability, composition and specific constituents. For instance, there are known transgenic plants with an elevated starch content or altered starch quality, or those with a different fatty acid composition in the harvested material.

It is preferable with a view to transgenic crops to use the compounds of the invention in economically important transgenic crops of useful plants and ornamentals, for example of cereals such as wheat, barley, rye, oats, millet, rice and corn or else crops of sugar beet, cotton, soybean, oilseed rape, potato, manioc, tomato, peas and other vegetables.

Preferably, the compounds of the invention can be used as herbicides in crops of useful plants which are resistant, or have been made resistant by genetic engineering, to the phytotoxic effects of the herbicides.

Conventional ways of producing novel plants which have modified properties in comparison to existing plants consist, for example, in traditional cultivation methods and the generation of mutants. Alternatively, novel plants with modified properties can be generated with the aid of recombinant methods (see, for example, EP-A-0221044, EP-A-0131624). For example, there have been descriptions in several cases of:

genetic modifications of crop plants for the purpose of modifying the starch synthesized in the plants (e.g. WO 92/11376, WO 92/14827, WO 91/19806), transgenic crop plants which are resistant to particular herbicides of the glufosinate type (cf., for example, EP-A-0242236, EP-A-242246) or glyphosate type (WO 92/00377) or the sulfonylurea type (EP-A-0257993, U.S. Pat. No. 5,013,659), transgenic crop plants, for example cotton, capable of producing *Bacillus thuringiensis* toxins (Bt toxins), which make the plants resistant to particular pests (EP-A-0142924, EP-A-0193259), transgenic crop plants with a modified fatty acid composition (WO 91/13972), genetically modified crop plants with novel constituents or secondary metabolites, for example novel phytoalexins, which bring about an increased disease resistance (EPA 309862, EPA0464461), genetically modified plants having reduced photorespiration, which have higher yields and higher stress tolerance (EPA 0305398), transgenic crop plants which produce pharmaceutically or diagnostically important proteins ("molecular pharming"), transgenic crop plants which feature higher yields or better quality, transgenic crop plants which feature a combination, for example, of the abovementioned novel properties ("gene stacking").

Numerous molecular biology techniques which can be used to produce novel transgenic plants with modified properties are known in principle; see, for example, I. Potrykus and G. Spangenberg (eds.) Gene Transfer to Plants, Springer Lab Manual (1995), Springer Verlag Berlin, Heidelberg, or Christou, "Trends in Plant Science" 1 (1996) 423-431).

For such recombinant manipulations, nucleic acid molecules which allow mutagenesis or sequence alteration by recombination of DNA sequences can be introduced into plasmids. With the aid of standard methods, it is possible, for example, to undertake base exchanges, remove parts of sequences or add natural or synthetic sequences. To join the DNA fragments with one another, adapters or linkers can be placed onto the fragments, see e.g. Sambrook et al., 1989, Molecular Cloning, A Laboratory Manual, 2nd edition Cold Spring Harbor Laboratory Press, Cold Spring Harbor, N.Y., or Winnacker "Gene und Klone [Genes and clones]", VCH Weinheim 2nd edition 1996.

For example, the generation of plant cells with a reduced activity of a gene product can be achieved by expressing at least one corresponding antisense RNA, a sense RNA for achieving a cosuppression effect, or by expressing at least one suitably constructed ribozyme which specifically cleaves transcripts of the abovementioned gene product. To this end, it is firstly possible to use DNA molecules which encompass the entire coding sequence of a gene product inclusive of any flanking sequences which may be present, and also DNA molecules which only encompass portions of the coding sequence, in which case it is necessary for these portions to be long enough to have an antisense effect in the cells. It is also possible to use DNA sequences which have a high degree of homology to the coding sequences of a gene product, but are not completely identical to them.

When expressing nucleic acid molecules in plants, the protein synthesized may be localized in any desired compartment of the plant cell. However, to achieve localization in a particular compartment, it is possible, for example, to join the coding region to DNA sequences which ensure localization in a particular compartment. Such sequences are known to those skilled in the art (see, for example, Braun et al., EMBO J. 11 (1992), 3219-3227; Wolter et al., Proc. Natl. Acad. Sci. USA 85 (1988), 846-850; Sonnewald et al., Plant J. 1 (1991), 95-106). The nucleic acid molecules can also be expressed in the organelles of the plant cells.

The transgenic plant cells can be regenerated by known techniques to give rise to entire plants. In principle, the transgenic plants may be plants of any desired plant species, i.e. not only monocotyledonous but also dicotyledonous plants.

Thus, transgenic plants can be obtained whose properties are altered by overexpression, suppression or inhibition of homologous (=natural) genes or gene sequences or expression of heterologous (=foreign) genes or gene sequences.

The compounds of the invention can be used with preference in transgenic crops which are resistant to growth regulators, for example dicamba, or to herbicides which inhibit essential plant enzymes, for example acetolactate synthases (ALS), EPSP synthases, glutamine synthases (GS) or hydroxyphenylpyruvate dioxygenases (HPPD), or to herbicides from the group of the sulfonylureas, the glyphosates, glufosinates or benzoylisoxazoles and analogous active ingredients.

When the active ingredients of the invention are used in transgenic crops, not only do the effects toward harmful plants which are observed in other crops occur, but often also effects which are specific to application in the particular transgenic crop, for example an altered or specifically widened spectrum of weeds which can be controlled, altered application rates which can be used for the application, preferably good combinability with the herbicides to which the transgenic crop is resistant, and influencing of growth and yield of the transgenic crop plants.

The invention therefore also provides for the use of the compounds of the invention as herbicides for control of harmful plants in transgenic crop plants.

The compounds of the invention can be applied in the form of wettable powders, emulsifiable concentrates, sprayable solutions, dusting products or granules in the customary formulations. The invention therefore also provides herbicidal and plant-growth-regulating compositions which comprise the compounds of the invention.

The compounds of the invention can be formulated in various ways, according to the biological and/or physicochemical parameters required. Possible formulations include, for example: wettable powders (WP), water-soluble powders (SP), water-soluble concentrates, emulsifiable concentrates (EC), emulsions (EW), such as oil-in-water and water-in-oil emulsions, sprayable solutions, suspension concentrates (SC), dispersions based on oil or water, oil-miscible solutions, capsule suspensions (CS), dusting products (DP), dressings, granules for scattering and soil application, granules (GR) in the form of microgranules, spray granules, absorption and adsorption granules, water-dispersible granules (WG), water-soluble granules (SG), ULV formulations, microcapsules and waxes.

These individual formulation types are known in principle and are described, for example, in: Winnacker-Küchler, "Chemische Technologie" [Chemical Technology], volume 7, C. Hanser Verlag Munich, 4th Ed. 1986, Wade van Valkenburg, "Pesticide Formulations", Marcel Dekker, N.Y., 1973, K. Martens, "Spray Drying" Handbook, 3rd Ed. 1979, G. Goodwin Ltd. London.

The formulation auxiliaries required, such as inert materials, surfactants, solvents and further additives, are likewise known and are described, for example, in: Watkins, "Handbook of Insecticide Dust Diluents and Carriers", 2nd ed., Darland Books, Caldwell N. J., H. v. Olphen, "Introduction to Clay Colloid Chemistry", 2nd ed., J. Wiley & Sons, N.Y., C. Marsden, "Solvents Guide", 2nd ed., Interscience, N.Y. 1963, McCutcheon's "Detergents and Emulsifiers Annual", MC Publ. Corp., Ridgewood N.J., Sisley and Wood, "Encyclopedia of Surface Active Agents", Chem. Publ. Co. Inc., N.Y. 1964, Schönfeldt, "Grenzflächenaktive Äthylenoxidaddukte" [Interface-active Ethylene Oxide Adducts], Wiss. Verlagsgesell., Stuttgart 1976, Winnacker-Küchler, "Chemische Technologie", Volume 7, C. Hanser Verlag Munich, 4th ed. 1986.

On the basis of these formulations, it is also possible to produce combinations with other pesticidally active substances, for example insecticides, acaricides, herbicides, fungicides, and also with safeners, fertilizers and/or growth regulators, for example in the form of a finished formulation or as a tankmix. Suitable safeners are, for example, mefenpyr-diethyl, cyprosulfamide, isoxadifen-ethyl, cloquintocet-mexyl and dichlormid.

Wettable powders are preparations which can be dispersed uniformly in water and, in addition to the active ingredient, apart from a diluent or inert substance, also comprise surfactants of the ionic and/or nonionic type (wetting agents, dispersants), for example polyethoxylated alkylphenols, polyethoxylated fatty alcohols, polyethoxylated fatty amines, fatty alcohol polyglycol ether sulfates, alkanesulfonates, alkylbenzenesulfonates, sodium lignosulfonate, sodium 2,2'-dinaphthylmethane-6,6'-disulfonate, sodium dibutylnaphthalenesulfonate or else sodium oleoylmethyltaurate. To produce the wettable powders, the herbicidally active ingredients are finely ground, for example in customary apparatuses such as hammer mills, blower mills and air-jet mills, and simultaneously or subsequently mixed with the formulation auxiliaries.

Emulsifiable concentrates are produced by dissolving the active ingredient in an organic solvent, for example butanol, cyclohexanone, dimethylformamide, xylene, or else relatively high-boiling aromatics or hydrocarbons or mixtures of the organic solvents, with addition of one or more ionic and/or nonionic surfactants (emulsifiers). Examples of emulsifiers which may be used are: calcium alkylarylsulfonates such as calcium dodecylbenzenesulfonate, or nonionic emulsifiers such as fatty acid polyglycol esters, alkylaryl polyglycol ethers, fatty alcohol polyglycol ethers, propylene oxide-ethylene oxide condensation products, alkyl polyethers, sorbitan esters, for example sorbitan fatty acid esters, or polyoxyethylene sorbitan esters, for example polyoxyethylene sorbitan fatty acid esters.

Dustable powders are obtained by grinding the active ingredient with finely distributed solid substances, for example talc, natural clays such as kaolin, bentonite and pyrophyllite, or diatomaceous earth.

Suspension concentrates may be water- or oil-based. They may be prepared, for example, by wet-grinding by means of commercial bead mills and optional addition of surfactants as have, for example, already been listed above for the other formulation types.

Emulsions, for example oil-in-water emulsions (EW), can be produced, for example, by means of stirrers, colloid mills and/or static mixers using aqueous organic solvents and optionally surfactants as already listed above, for example, for the other formulation types.

Granules can be prepared either by spraying the active ingredient onto adsorptive granular inert material or by applying active ingredient concentrates to the surface of carriers, such as sand, kaolinites or granular inert material, by means of adhesives, for example polyvinyl alcohol, sodium polyacrylate or else mineral oils. Suitable active ingredients can also be granulated in the manner customary for the production of fertilizer granules—if desired as a mixture with fertilizers.

Water-dispersible granules are produced generally by the customary processes such as spray-drying, fluidized bed granulation, pan granulation, mixing with high-speed mixers and extrusion without solid inert material.

For the production of pan, fluidized-bed, extruder and spray granules, see e.g. processes in "Spray Drying Handbook" 3rd Ed. 1979, G. Goodwin Ltd., London, J. E. Browning, "Agglomeration", Chemical and Engineering 1967, pages 147 ff.; "Perry's Chemical Engineer's Handbook", 5th ed., McGraw-Hill, New York 1973, pp. 8-57.

For further details regarding the formulation of crop protection compositions, see, for example, G. C. Klingman, "Weed Control as a Science", John Wiley and Sons, Inc., New York, 1961, pages 81-96 and J. D. Freyer, S. A. Evans, "Weed Control Handbook", 5th Ed., Blackwell Scientific Publications, Oxford, 1968, pages 101-103.

The agrochemical preparations contain generally 0.1 to 99% by weight, especially 0.1 to 95% by weight, of compounds of the invention.

In wettable powders, the active ingredient concentration is, for example, about 10% to 90% by weight, the remainder to 100% by weight consisting of customary formulation constituents. In emulsifiable concentrates, the active ingredient concentration may be about 1% to 90% and preferably 5% to 80% by weight. Dust-type formulations contain 1% to 30% by weight of active ingredient, preferably usually 5% to 20% by weight of active ingredient; sprayable solutions contain about 0.05% to 80% by weight, preferably 2% to 50% by weight of active ingredient. In the case of water-dispersible granules, the active ingredient content depends partially on whether the active compound is present in liquid or solid form and on which granulation auxiliaries, fillers, etc., are used. In the water-dispersible granules, the content of active ingredient is, for example, between 1% and 95% by weight, preferably between 10% and 80% by weight.

In addition, the active ingredient formulations mentioned optionally comprise the respective customary stickers, wetters, dispersants, emulsifiers, penetrants, preservatives, antifreeze agents and solvents, fillers, carriers and dyes, defoamers, evaporation inhibitors and agents which influence the pH and the viscosity.

For application, the formulations in commercial form are, if appropriate, diluted in a customary manner, for example in the case of wettable powders, emulsifiable concentrates, dispersions and water-dispersible granules with water. Dust-type preparations, granules for soil application or granules for scattering and sprayable solutions are not normally diluted further with other inert substances prior to application.

The required application rate of the compounds of the formula (I) varies with the external conditions, including temperature, humidity and the type of herbicide used. It can vary within wide limits, for example between 0.001 and 1.0 kg/ha or more of active substance, but it is preferably between 0.005 and 750 g/ha.

The examples below illustrate the invention.

A. Chemical Examples

Synthesis of N-(1-methyltetrazol-5-yl)-3-chloro-4-(methylthio)-5,6,7,8-tetrahydronaphthalene-2-carboxamide (no. 1-36)

Step 1: Synthesis of methyl 3-amino-4-(methylthio)-5,6,7,8-tetrahydronaphthalene-2-carboxylate 11.66 g (120 mmol) of potassium thiocyanate in 120 mL of methanol under an argon atmosphere were cooled down to a temperature of −10° C. At this temperature, 7.19 g (45 mmol) of bromine were added. Subsequently, 6.16 g (30 mmol) of methyl 3-amino-5,6,7,8-tetrahydronaphthalene-2-carboxylate were added. The reaction mixture was stirred without cooling for 1.5 h and then cooled down to 0° C. After addition of 7.46 g (54 mmol) of potassium carbonate, 11.52 g (48 mmol) of sodium sulfide nonahydrate, dissolved in 40 mL of water, were added dropwise. In the course of this, the temperature increased to 7° C. The mixture was stirred while cooling with an ice bath for another 30 min and then 8.70 g (69 mmol) of dimethyl sulfate were added dropwise. After stirring at 0° C. for one hour, 5 mL of dimethylamine solution (60% in water) were added and the mixture was stirred at room temperature for a further 30 min.

For workup, the mixture was poured onto 300 mL of ice-water and filtered with suction, and the precipitate was washed with 100 mL of ice-water. The residue was dried in vacuo. 7.17 g of methyl 3-amino-4-(methylthio)-5,6,7,8-tetrahydronaphthalene-2-carboxylate were obtained. $^1$H-NMR (DMSO-$d_6$): 7.53 (s, 1H), 6.74 (bs, 2H), 3.79 (s, 3H), 2.93 (t, 2H), 2.61 (t, 2H), 2.16 (s, 3H), 1.83-1.70 (m, 4H).

Step 2: Synthesis of methyl 3-chloro-4-(methylthio)-5,6,7,8-tetrahydronaphthalene-2-carboxylate To a mixture of 3.50 g (13.9 mmol) of methyl 3-amino-4-(methylthio)-5,6,7,8-tetrahydronaphthalene-2-carboxylate and 2.81 g (21 mmol) of copper(II) chloride in 110 mL of acetonitrile were added dropwise, at 70° C., 1.79 g (15 mmol) of isoamyl nitrite. Subsequently, the mixture was stirred at 80° C. for another 30 min. After cooling to RT, the mixture was diluted with ethyl acetate and washed successively with 2 N hydrochloric acid (3 x), saturated aqueous sodium hydrogencarbonate solution and sodium chloride solution. The organic phase was dried and the filtrate was freed of solvents. The residue was purified by means of LC (toluene). 3.09 g of methyl 3-chloro-4-(methylthio)-5,6,7,8-tetrahydronaphthalene-2-carboxylate were obtained. $^1$H-NMR (DMSO-$d_6$): 7.45 (s, 1H), 3.84 (s, 3H), 3.00 (t, 2H), 2.74 (t, 2H), 2.30 (s, 3H), 1.80-1.66 (m, 4H).

Step 3: Synthesis of 3-chloro-4-(methylthio)-5,6,7,8-tetrahydronaphthalene-2-carboxylic acid 271 mg (1 mmol) of methyl 3-chloro-4-(methylthio)-5,6,7,8-tetrahydronaphthalene-2-carboxylate and 2 mL of 2 N sodium hydroxide solution in 3 mL of methanol were heated to 50° C. for 3 h. After cooling to RT, the mixture was acidified with 2 N hydrochloric acid, and the precipitated crystals were filtered off with suction, washed with water and dried under reduced pressure. 230 mg of 3-chloro-4-(methylthio)-5,6,7,8-tetrahydronaphthalene-2-carboxylic acid were obtained. $^1$H-NMR (DMSO-$d_6$): 7.41 (s, 1H), 2.99 (t, 2H), 2.74 (t, 2H), 2.30 (s, 3H), 1.79-1.66 (m, 4H).

Step 4: N-(1-Methyltetrazol-5-yl)-3-chloro-4-(methylthio)-5,6,7,8-tetrahydronaphthalene-2-carboxamide (no. 1-36)

218 mg (0.85 mmol) of 3-chloro-4-(methylthio)-5,6,7,8-tetrahydronaphthalene-2-carboxylic acid and 129 mg (1.27 mmol) of 5-amino-1-methyltetrazole were dissolved in 2 mL of pyridine. Subsequently, at 0° C., 155 mg (1.27 mmol) of thionyl chloride were added dropwise. After 4 d at RT, the mixture was acidified with 2 N hydrochloric acid and taken up with ethyl acetate, the phases were separated and the organic phase was washed with saturated aqueous sodium hydrogencarbonate solution and sodium chloride solution. The organic phase was dried and the filtrate was freed of solvents. 170 mg of N-(1-methyltetrazol-5-yl)-3-chloro-4-(methylthio)-5,6,7,8-tetrahydronaphthalene-2-carboxamide were obtained.

The examples listed in the tables below were prepared analogously to the abovementioned methods or are obtainable analogously to the abovementioned methods. The compounds listed in the tables below are very particularly preferred.

The abbreviations used mean:

Et=ethyl Me=methyl nPr=n-propyl cPr=cyclopropyl

TABLE 1

Inventive compounds of the general formula (I) in which Q is $Q^1$ and $Z^4$ is a direct bond

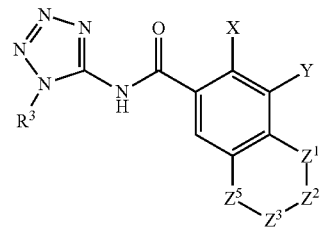

| No. | $R^3$ | X | Y | $Z^1$ | $Z^2$ | $Z^3$ | $Z^5$ | Physical data ($^1$H NMR, DMSO-$d_6$, 400 MHz) |
|---|---|---|---|---|---|---|---|---|
| 1-1 | Me | Me | Cl | $CH_2$ | $CH_2$ | bond | $CH_2$ | |
| 1-2 | Et | Me | Cl | $CH_2$ | $CH_2$ | bond | $CH_2$ | |
| 1-3 | nPr | Me | Cl | $CH_2$ | $CH_2$ | bond | $CH_2$ | |
| 1-4 | Me | Et | Cl | $CH_2$ | $CH_2$ | bond | $CH_2$ | |
| 1-5 | Et | Et | Cl | $CH_2$ | $CH_2$ | bond | $CH_2$ | |
| 1-6 | Me | nPr | Cl | $CH_2$ | $CH_2$ | bond | $CH_2$ | |
| 1-7 | Me | cPr | Cl | $CH_2$ | $CH_2$ | bond | $CH_2$ | |
| 1-8 | Me | Me | SMe | $CH_2$ | $CH_2$ | bond | $CH_2$ | 7.53 (s, 1H), 4.16 (s, 3H), 2.92-2.88 (m, 4H), 2.30 (s, 3H), 2.09 (s, 3H), 2.02-1.96 (m, 2H) |
| 1-9 | Me | Me | SOMe | $CH_2$ | $CH_2$ | bond | $CH_2$ | 7.74 (s, 1H), 4.18 (s, 3H), 3.27-2.97 (m, 2H), 2.82 (t, 2H), 2.67 (s, 3H), 2.24 (s, 3H), 2.02 (m, 2H) |
| 1-10 | Me | Me | $SO_2$Me | $CH_2$ | $CH_2$ | bond | $CH_2$ | 7.87 (s, 1H), 4.21 (s, 3H), 3.18 (t, 2H), 3.11 (s, 3H), 2.88 (t, 2H), 2.45 (s, 3H), 1.99 (m, 2H) |
| 1-11 | Me | Me | SEt | $CH_2$ | $CH_2$ | bond | $CH_2$ | |
| 1-12 | Me | Me | SOEt | $CH_2$ | $CH_2$ | bond | $CH_2$ | |
| 1-13 | Me | Me | $SO_2$Et | $CH_2$ | $CH_2$ | bond | $CH_2$ | |
| 1-14 | Me | Cl | Cl | $CH_2$ | $CH_2$ | bond | $CH_2$ | |

TABLE 1-continued

Inventive compounds of the general formula (I) in which Q is $Q^1$ and $Z^4$ is a direct bond

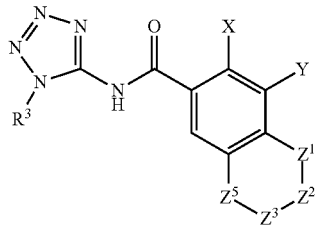

| No. | $R^3$ | X | Y | $Z^1$ | $Z^2$ | $Z^3$ | $Z^5$ | Physical data ($^1$H NMR, DMSO-$d_6$, 400 MHz) |
|---|---|---|---|---|---|---|---|---|
| 1-15 | Et | Cl | Cl | $CH_2$ | $CH_2$ | bond | $CH_2$ | |
| 1-16 | nPr | Cl | Cl | $CH_2$ | $CH_2$ | bond | $CH_2$ | |
| 1-17 | Me | Cl | Br | $CH_2$ | $CH_2$ | bond | $CH_2$ | |
| 1-18 | Me | Cl | SMe | $CH_2$ | $CH_2$ | bond | $CH_2$ | 11.68 (bs, 1H), 7.56 (s, 1H), 4.01 (s, 3H), 3.12 (t, 2H), 2.99 (t, 2H), 2.42 (s, 3H), 2.14-2.07 (m, 2H) |
| 1-19 | Me | Cl | SOMe | $CH_2$ | $CH_2$ | bond | $CH_2$ | 11.77 (bs, 1H), 7.76 (s, 1H), 3.99 (s, 3H), 3.52-3.46 (m, 1H), 3.29-3.22 (m, 1H), 2.93 (s, 3H), 2.88 (t, 2H), 2.14-2.08 (m, 2H) |
| 1-20 | Me | Cl | $SO_2Me$ | $CH_2$ | $CH_2$ | bond | $CH_2$ | 11.88 (bs, 1H), 7.92 (s, 1H), 4.01 (s, 3H), 3.40 (s, 3H), 3.39 (t, 2H), 2.95 (t, 2H), 2.10-2.02 (m, 2H) |
| 1-21 | Me | Cl | SEt | $CH_2$ | $CH_2$ | bond | $CH_2$ | 11.7 (bs, 1H), 7.54 (s, 1H), 3.98 (s, 3H), 3.08 (t, 2H), 2.98 (t, 2H), 2.89 (q, 2H), 2.08 (m, 2H), 1.13 (t, 3H) |
| 1-22 | Me | Cl | SOEt | $CH_2$ | $CH_2$ | bond | $CH_2$ | 11.77 (bs, 1H), 7.76 (s, 1H), 3.99 (s, 3H), 3.53-3.44 (m, 1H), 3.22-3.08 (m, 3H), 2.88 (t, 2H), 2.09 (m, 2H), 1.23 (t, 3H) |
| 1-23 | Me | Cl | $SO_2Et$ | $CH_2$ | $CH_2$ | bond | $CH_2$ | 11.85 (bs, 1H), 7.91 (s, 1H), 4.00 (s, 3H), 3.50 (q, 2H), 3.37 (t, 2H), 2.95 (t, 2H), 2.07 (m, 2H), 1.18 (t, 3H) |
| 1-24 | Et | Cl | SMe | $CH_2$ | $CH_2$ | bond | $CH_2$ | 11.6 (bs, 1H), 7.49 (s, 1H), 4.32 (q, 2H), 3.09 (t, 2H), 2.96 (t, 2H), 2.39 (s, 3H), 2.08 (m, 2H), 1.45 (t, 3H) |
| 1-25 | Et | Cl | SOMe | $CH_2$ | $CH_2$ | bond | $CH_2$ | 11.68 (bs, 1H), 7.74 (s, 1H), 4.34 (q, 2H), 3.53-3.21 (m, 2H), 2.93 (s, 3H), 2.89 (t, 2H), 2.11 (m, 2H), 1.46 (t, 3H) |
| 1-26 | Et | Cl | $SO_2Me$ | $CH_2$ | $CH_2$ | bond | $CH_2$ | 11.76 (bs, 1H), 7.89 (s, 1H), 4.37 (q, 2H), 3.40 (s, 3H), 3.37 (t, 2H), 2.95 (t, 2H), 2.07 (m, 2H), 1.48 (t, 3H) |
| 1-27 | Et | Cl | SEt | $CH_2$ | $CH_2$ | bond | $CH_2$ | 11.6 (bs, 1H), 7.53 (S, 1h), 4.34 (q, 2H), 3.08 (t, 2H), 2.98 (t, 2H) 2.89 (q, 2H), 2.08 (m, 2H), 1.46 (t, 3H), 1.11 (t, 3H) |
| 1-28 | Et | Cl | SOEt | $CH_2$ | $CH_2$ | bond | $CH_2$ | 11.67 (bs, 1H), 7.75 (s, 1H), 4.35 (q, 2H), 3.52-3.44 (m, 2H), 3.22-3.09 (m, 3H), 2.88 (t, 2H), 2.08 (m, 2H), 1.46 (t, 3H), 1.23 (t, 3H) |
| 1-29 | Et | Cl | $SO_2Et$ | $CH_2$ | $CH_2$ | bond | $CH_2$ | 11.76 (bs, 1H), 7.90 (s, 1H), 4.36 (q, 2H), 3.50 (q, 2H), 3.37 (t, 2H), 2.96 (t, 2H), 2.06 (m, 2H), 1.47 (t, 3H), 1.18 (t, 3H) |
| 1-30 | Me | Cl | SMe | CO | $CH_2$ | bond | $CH_2$ | 11.93 (bs, 1H), 7.85 (s, 1H), 4.02 (s, 3H), 3.10 (m, 2H), 2.77 (m, 2H), 2.50 (s, 3H) |
| 1-31 | Me | Cl | SOMe | CO | $CH_2$ | bond | $CH_2$ | |
| 1-32 | Me | Cl | $SO_2Me$ | CO | $CH_2$ | bond | $CH_2$ | 7.92 (s, 1H), 4.17 (s, 3H), 3.51 (s, 3H), 3.22 (m, 2H), 2.92 (m, 2H) |
| 1-33 | Me | Cl | SEt | CO | $CH_2$ | bond | $CH_2$ | |
| 1-34 | Me | Cl | SOEt | CO | $CH_2$ | bond | $CH_2$ | |
| 1-35 | Me | Cl | $SO_2Et$ | CO | $CH_2$ | bond | $CH_2$ | |
| 1-36 | Me | Cl | SMe | $CF_2$ | $CH_2$ | bond | $CH_2$ | |
| 1-37 | Me | Cl | SOMe | $CF_2$ | $CH_2$ | bond | $CH_2$ | |
| 1-38 | Me | Cl | $SO_2Me$ | $CF_2$ | $CH_2$ | bond | $CH_2$ | |
| 1-39 | Et | Cl | SMe | $CF_2$ | $CH_2$ | bond | $CH_2$ | |

TABLE 1-continued

Inventive compounds of the general formula (I) in which Q is $Q^1$ and $Z^4$ is a direct bond

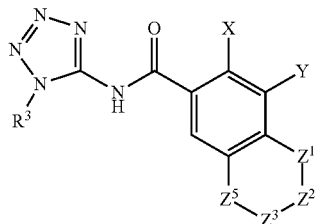

| No. | $R^3$ | X | Y | $Z^1$ | $Z^2$ | $Z^3$ | $Z^5$ | Physical data ($^1$H NMR, DMSO-$d_6$, 400 MHz) |
|---|---|---|---|---|---|---|---|---|
| 1-40 | Et | Cl | SOMe | $CF_2$ | $CH_2$ | bond | $CH_2$ | |
| 1-41 | Et | Cl | $SO_2Me$ | $CF_2$ | $CH_2$ | bond | $CH_2$ | |
| 1-42 | Me | Cl | SMe | CHMe | $CH_2$ | bond | $CH_2$ | 11.67 (bs, 1H), 7.55 (s, 1H), 3.99 (s, 3H), 3.58-3.50 (m, 1H), 3.14-3.04 (m, 1H), 2.92-2.84 (m1H), 2.42 (s, 3H), 2.32-2.22 (m, 1H), 1.86-78 (m, 1H) |
| 1-43 | Me | Cl | SOMe | CHMe | $CH_2$ | bond | $CH_2$ | |
| 1-44 | Me | Cl | $SO_2Me$ | CHMe | $CH_2$ | bond | $CH_2$ | |
| 1-45 | Me | Cl | SMe | $CMe_2$ | $CH_2$ | bond | $CH_2$ | |
| 1-46 | Me | Cl | SOMe | $CMe_2$ | $CH_2$ | bond | $CH_2$ | |
| 1-47 | Me | Cl | $SO_2Me$ | $CME_2$ | $CH_2$ | bond | $CH_2$ | |
| 1-48 | Et | Cl | SMe | $CMe_2$ | $CH_2$ | bond | $CH_2$ | |
| 1-49 | Et | Cl | SOMe | $CMe_2$ | $CH_2$ | bond | $CH_2$ | |
| 1-50 | Et | Cl | $SO_2Me$ | $CMe_2$ | $CH_2$ | bond | $CH_2$ | |
| 1-51 | Me | Cl | SMe | $CH_2$ | $CH_2$ | $CH_2$ | $CH_2$ | 7.43 (s, 1H), 3.97 (s, 3H), 3.02 (t, 2H), 2.78 (t, 2H), 2.32 (s, 3H), 1.84-1.66 (m, 4H) |
| 1-52 | Me | Cl | SOMe | $CH_2$ | $CH_2$ | $CH_2$ | $CH_2$ | 11.75 (bs, 1H), 7.59 (s, 1H), 3.99 (s, 3H), 3.45-3.35 (m, 1H), 3.10-3.00 (m, 1H), 3.03 (s, 3H), 1.78-1.72 (m, 4H) |
| 1-53 | Me | Cl | $SO_2Me$ | $CH_2$ | $CH_2$ | $CH_2$ | $CH_2$ | 11.84 (bs, 1H), 7.74 (s, 1H), 4.00 (s, 3H), 3.42 (s, 3H), 3.25 (m, 2H), 2.86 (m, 2H), 1.71 (m, 4H) |
| 1-54 | Me | Cl | SEt | $CH_2$ | $CH_2$ | $CH_2$ | $CH_2$ | |
| 1-55 | Me | Cl | SOEt | $CH_2$ | $CH_2$ | $CH_2$ | $CH_2$ | |
| 1-56 | Me | Cl | $SO_2Et$ | $CH_2$ | $CH_2$ | $CH_2$ | $CH_2$ | |
| 1-57 | Et | Cl | SMe | $CH_2$ | $CH_2$ | $CH_2$ | $CH_2$ | |
| 1-58 | Et | Cl | SOMe | $CH_2$ | $CH_2$ | $CH_2$ | $CH_2$ | |
| 1-59 | Et | Cl | $SO_2Me$ | $CH_2$ | $CH_2$ | $CH_2$ | $CH_2$ | |
| 1-60 | Et | Cl | SEt | $CH_2$ | $CH_2$ | $CH_2$ | $CH_2$ | |
| 1-61 | Et | Cl | SOEt | $CH_2$ | $CH_2$ | $CH_2$ | $CH_2$ | |
| 1-62 | Et | Cl | $SO_2Et$ | $CH_2$ | $CH_2$ | $CH_2$ | $CH_2$ | |
| 1-63 | Me | Cl | SMe | O | $CH_2$ | bond | $CH_2$ | 11.57 (bs, 1H), 7.53 (s, 1H), 4.73 (t, 2H), 3.97 (s, 3H), 3.28 (t, 2H), 2.43 (s, 3H) |
| 1-64 | Me | Cl | SOMe | O | $CH_2$ | bond | $CH_2$ | 7.73 (s, 1H), 4.82 (t, 2H), 3.93 (s, 3H), 3.26 (t, 2H), 3.05 (s, 3H) |
| 1-65 | Me | Cl | $SO_2Me$ | O | $CH_2$ | bond | $CH_2$ | 11.74 (bs, 1H), 7.83 (s, 1H), 4.82 (t, 2H), 3.99 (s, 3H), 3.37 (s, 3H), 3.27 (t, 2H) |
| 1-66 | Me | Cl | SMe | $CH_2$ | O | bond | $CH_2$ | |
| 1-67 | Me | Cl | SOMe | $CH_2$ | O | bond | $CH_2$ | |
| 1-68 | Me | Cl | $SO_2Me$ | $CH_2$ | O | bond | $CH_2$ | |
| 1-69 | Me | Cl | SMe | $CH_2$ | $CH_2$ | bond | O | 11.69 (bs, 1H), 7.12 (s, 1H), 4.65 (t, 2H), 3.98 (s, 3H), 3.41 (t, 2H), 2.45 (s, 3H) |
| 1-70 | Me | Cl | SOMe | $CH_2$ | $CH_2$ | bond | O | 7.31 (s, 1H), 4.69 (t, 2H), 3.98 (s, 3H), 3.5-3.45 (m, 2H), 2.95 (s, 3H) |
| 1-71 | Me | Cl | $SO_2Me$ | $CH_2$ | $CH_2$ | bond | O | 11.87 (bs, 1H), 7.51 (s, 1H), 4.67 (t, 2H), 4.01 (s, 3H), 3.66 (t, 2H), 3.42 (s, 3H) |
| 1-72 | Me | Cl | SMe | O | $CH_2$ | bond | O | |
| 1-73 | Me | Cl | SOMe | O | $CH_2$ | bond | O | |
| 1-74 | Me | Cl | $SO_2Me$ | O | $CH_2$ | bond | O | |
| 1-75 | Me | Br | SMe | $CH_2$ | $CH_2$ | bond | $CH_2$ | 11.77 (bs, 1H), 7.46 (s, 1H), 3.98 (s, 3H), 3.12 (t, 2H), 2.94 (t, 2H), 2.39 (s, 3H), 2.11-2.03 (m, 2H) |

TABLE 1-continued

Inventive compounds of the general formula (I) in which Q is $Q^1$ and $Z^4$ is a direct bond

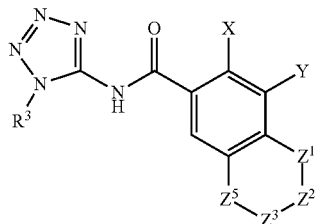

| No. | $R^3$ | X | Y | $Z^1$ | $Z^2$ | $Z^3$ | $Z^5$ | Physical data ($^1$H NMR, DMSO-$d_6$, 400 MHz) |
|---|---|---|---|---|---|---|---|---|
| 1-76 | Me | Br | SOMe | $CH_2$ | $CH_2$ | bond | $CH_2$ | 11.75 (bs, 1H), 7.71 (s, 1H), 4.01 (s, 3H), 3.55-3.47 (m, 1H), 3.28-3.20 (m, 1H), 2.91 (s, 3H) 2.10 (m, 2H) |
| 1-77 | Me | Br | $SO_2$Me | $CH_2$ | $CH_2$ | bond | $CH_2$ | 11.84 (bs, 1H), 7.84 (s, 1H), 4.03 (s, 3H), 3.41 (t, 2H), 3.40 (s, 3H), 2.93 (t, 2H), 2.05 (m, 2H) |
| 1-78 | Me | Br | SEt | $CH_2$ | $CH_2$ | bond | $CH_2$ | 11.85 (bs, 1H), 7.48 (s, 1H), 3.99 (s, 3H), 3.10 (t, 2H), 2.95 (t, 2H), 2.89 (q, 2H), 2.07 (m, 2H), 1.14 (t, 3H) |
| 1-79 | Me | Br | SOEt | $CH_2$ | $CH_2$ | bond | $CH_2$ | 11.78 (bs, 1H), 7.71 (s, 1H), 4.01 (s, 3H), 3.55-3.47 (m, 1H), 3.23-3.09 (m, 3H), 2.85 (t, 2H), 2.08 (m, 2H), 1.25 (t, 3H) |
| 1-80 | Me | Br | $SO_2$Et | $CH_2$ | $CH_2$ | bond | $CH_2$ | 11.84 (bs, 1H), 7.85 (s, 1H), 4.03 (s, 3H), 3.52 (q, 2H), 3.39 (t, 2H), 2.93 (t, 2H), 2.05 (m, 2H), 1.19 (t, 3H) |
| 1-81 | Et | Br | SMe | $CH_2$ | $CH_2$ | bond | $CH_2$ | |
| 1-82 | Et | Br | SOMe | $CH_2$ | $CH_2$ | bond | $CH_2$ | |
| 1-83 | Et | Br | $SO_2$Me | $CH_2$ | $CH_2$ | bond | $CH_2$ | |
| 1-84 | Et | Br | SEt | $CH_2$ | $CH_2$ | bond | $CH_2$ | 11.7 (bs, 1H), 7.47 (s, 1H), 4.36 (q, 2H), 3.10 (t, 2H), 2.96 (t, 2H), 2.89 (q, 2H), 2.06 (m, 2H), 1.46 (t, 3H), 1.14 (t, 3H) |
| 1-85 | Et | Br | SOEt | $CH_2$ | $CH_2$ | bond | $CH_2$ | 11.66 (bs, 1H), 7.70 (s, 1H), 4.36 (q, 2H), 3.55-3.47 (m, 2H), 3.22-3.09 (m, 3H), 2.86 (t, 2H), 2.08 (m, 2H), 1.47 (t, 3H), 1.25 (t, 3H) |
| 1-86 | Et | Br | $SO_2$Et | $CH_2$ | $CH_2$ | bond | $CH_2$ | 11.74 (bs, 1H), 7.84 (s, 1H), 4.38 (q, 2H), 3.52 (q, 2H), 3.38 (t, 2H), 2.94 (t, 2H), 2.05 (m, 2H), 1.48 (t, 3H), 1.19 (t, 3H) |
| 1-87 | Me | Me | F | $SO_2$ | $CH_2$ | bond | $CH_2$ | 11.82 (bs, 1H), 7.67 (s, 1H), 3.99 (s, 3H), 3.76 (t, 2H), 3.41 (t, 2H), 2.36 (d, 3H) |
| 1-88 | Me | Me | SMe | $SO_2$ | $CH_2$ | bond | $CH_2$ | 11.05 (bs, 1H), 7.81 (s, 1H), 4.13 (s, 3H), 3.59 (t, 2H), 3.42 (t, 2H), 2.77 (s, 3H), 2.46 (s, 3H) |
| 1-89 | Me | Me | SOMe | $SO_2$ | $CH_2$ | bond | $CH_2$ | 7.93 (s, 1H), 4.01 (s, 3H), 3.76-3.66 (m, 2H), 3.41 (t, 2H), 3.03 (s, 3H), 2.77 (s, 3H) |
| 1-90 | Me | Me | $SO_2$Me | $SO_2$ | $CH_2$ | bond | $CH_2$ | 8.10 (s, 1H), 4.02 (s, 3H), 3.66 (t, 2H), 3.41 (t, 2H), 3.40 (s, 3H), 2.72 (s, 3H) |
| 1-91 | Me | Me | SEt | $SO_2$ | $CH_2$ | bond | $CH_2$ | |
| 1-92 | Me | Me | SOEt | $SO_2$ | $CH_2$ | bond | $CH_2$ | |
| 1-93 | Me | Me | $SO_2$Et | $SO_2$ | $CH_2$ | bond | $CH_2$ | |
| 1-94 | Et | Me | SMe | $SO_2$ | $CH_2$ | bond | $CH_2$ | |
| 1-95 | Et | Me | SOMe | $SO_2$ | $CH_2$ | bond | $CH_2$ | |
| 1-96 | Et | Me | $SO_2$Me | $SO_2$ | $CH_2$ | bond | $CH_2$ | |
| 1-97 | Et | Me | SEt | $SO_2$ | $CH_2$ | bond | $CH_2$ | |
| 1-98 | Et | Me | SOEt | $SO_2$ | $CH_2$ | bond | $CH_2$ | |
| 1-99 | Et | Me | $SO_2$Et | $SO_2$ | $CH_2$ | bond | $CH_2$ | |
| 1-100 | Me | Me | OMe | $SO_2$ | $CH_2$ | bond | $CH_2$ | |
| 1-101 | Me | Me | OEt | $SO_2$ | $CH_2$ | bond | $CH_2$ | |
| 1-102 | Me | Me | $OC_2H_4$OMe | $SO_2$ | $CH_2$ | bond | $CH_2$ | |
| 1-103 | Me | Me | Pyrazol-1-yl | $SO_2$ | $CH_2$ | bond | $CH_2$ | 10.98 (bs, 1H), 7.85 (s, 1H), 7.77 (d, 1H), 7.73 (d, 1H), 6.56 (t, 1H), 4.11 (s, 3H), 3.54 (t, 2H), 3.43 (t, 2H), 2.23 (s, 3H) |

TABLE 1-continued

Inventive compounds of the general formula (I) in which Q is $Q^1$ and $Z^4$ is a direct bond

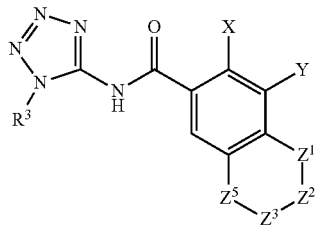

| No. | $R^3$ | X | Y | $Z^1$ | $Z^2$ | $Z^3$ | $Z^5$ | Physical data ($^1$H NMR, DMSO-$d_6$, 400 MHz) |
|---|---|---|---|---|---|---|---|---|
| 1-104 | Me | Cl | H | $SO_2$ | $CH_2$ | bond | $CH_2$ | |
| 1-105 | Me | Cl | Cl | $SO_2$ | $CH_2$ | bond | $CH_2$ | 11.98 (bs, 1H), 7.97 (s, 1H), 4.01 (s, 3H), 3.81 (t, 2H), 3.40 (t, 2H) |
| 1-106 | Me | Cl | SMe | $SO_2$ | $CH_2$ | bond | $CH_2$ | |
| 1-107 | Me | Cl | SOMe | $SO_2$ | $CH_2$ | bond | $CH_2$ | |
| 1-108 | Me | Cl | $SO_2Me$ | $SO_2$ | $CH_2$ | bond | $CH_2$ | |
| 1-109 | Me | Cl | SEt | $SO_2$ | $CH_2$ | bond | $CH_2$ | |
| 1-110 | Me | Cl | SOEt | $SO_2$ | $CH_2$ | bond | $CH_2$ | |
| 1-111 | Me | Cl | $SO_2Et$ | $SO_2$ | $CH_2$ | bond | $CH_2$ | |
| 1-112 | Et | Cl | SMe | $SO_2$ | $CH_2$ | bond | $CH_2$ | |
| 1-113 | Et | Cl | SOMe | $SO_2$ | $CH_2$ | bond | $CH_2$ | |
| 1-114 | Et | Cl | $SO_2Me$ | $SO_2$ | $CH_2$ | bond | $CH_2$ | |
| 1-115 | Et | Cl | SEt | $SO_2$ | $CH_2$ | bond | $CH_2$ | |
| 1-116 | Et | Cl | SOEt | $SO_2$ | $CH_2$ | bond | $CH_2$ | |
| 1-117 | Et | Cl | $SO_2Et$ | $SO_2$ | $CH_2$ | bond | $CH_2$ | |
| 1-118 | Me | Cl | OMe | $SO_2$ | $CH_2$ | bond | $CH_2$ | |
| 1-119 | Me | Cl | OEt | $SO_2$ | $CH_2$ | bond | $CH_2$ | |
| 1-120 | Me | Cl | $OC_2H_4OMe$ | $SO_2$ | $CH_2$ | bond | $CH_2$ | |
| 1-121 | Me | Cl | Pyrazol-1-yl | $SO_2$ | $CH_2$ | bond | $CH_2$ | |

TABLE 2

Inventive compounds of the general formula (I) in which Q is $Q^2$, in which $R^3$ is methyl, and $Z^4$ is a direct bond

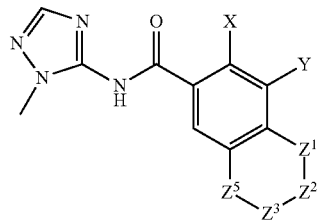

| No. | X | Y | $Z^1$ | $Z^2$ | $Z^3$ | $Z^5$ | Physical data ($^1$H NMR, DMSO-$d_6$, 400 MHz) |
|---|---|---|---|---|---|---|---|
| 2-1 | Me | Cl | $CH_2$ | $CH_2$ | bond | $CH_2$ | |
| 2-2 | Me | Cl | $CH_2$ | $CH_2$ | bond | $CH_2$ | |
| 2-3 | Me | Cl | $CH_2$ | $CH_2$ | bond | $CH_2$ | |
| 2-4 | Et | Cl | $CH_2$ | $CH_2$ | bond | $CH_2$ | |
| 2-5 | Et | Cl | $CH_2$ | $CH_2$ | bond | $CH_2$ | |
| 2-6 | nPr | Cl | $CH_2$ | $CH_2$ | bond | $CH_2$ | |
| 2-7 | cPr | Cl | $CH_2$ | $CH_2$ | bond | $CH_2$ | |
| 2-8 | Me | SMe | $CH_2$ | $CH_2$ | bond | $CH_2$ | |
| 2-9 | Me | SOMe | $CH_2$ | $CH_2$ | bond | $CH_2$ | |
| 2-10 | Me | $SO_2Me$ | $CH_2$ | $CH_2$ | bond | $CH_2$ | |
| 2-11 | Me | SEt | $CH_2$ | $CH_2$ | bond | $CH_2$ | |
| 2-12 | Me | SOEt | $CH_2$ | $CH_2$ | bond | $CH_2$ | |
| 2-13 | Me | $SO_2Et$ | $CH_2$ | $CH_2$ | bond | $CH_2$ | |
| 2-14 | Cl | Cl | $CH_2$ | $CH_2$ | bond | $CH_2$ | |
| 2-15 | Cl | Cl | $CH_2$ | $CH_2$ | bond | $CH_2$ | |
| 2-16 | Cl | Cl | $CH_2$ | $CH_2$ | bond | $CH_2$ | |
| 2-17 | Cl | Br | $CH_2$ | $CH_2$ | bond | $CH_2$ | |

TABLE 2-continued

Inventive compounds of the general formula (I) in which Q is $Q^2$, in which $R^3$ is methyl, and $Z^4$ is a direct bond

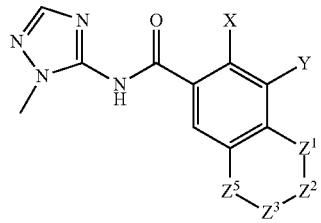

| No. | X | Y | $Z^1$ | $Z^2$ | $Z^3$ | $Z^5$ | Physical data ($^1$H NMR, DMSO-$d_6$, 400 MHz) |
|---|---|---|---|---|---|---|---|
| 2-18 | Cl | SMe | CH$_2$ | CH$_2$ | bond | CH$_2$ | 11.09 (bs, 1H), 7.88 (s1H), 7.48 (s, 1H), 3.76 (s, 3H), 3.09 (t, 2H), 2.96 (t, 2H), 2.40 (s, 3H), 2.08 (m, 2H) |
| 2-19 | Cl | SOMe | CH$_2$ | CH$_2$ | bond | CH$_2$ | |
| 2-20 | Cl | SO$_2$Me | CH$_2$ | CH$_2$ | bond | CH$_2$ | 11.28 (bs, 1H), 7.90 (s, 1H), 7.85 (s, 1H), 3.78 (s, 3H), 3.39 (s, 3H), 3.38 (t, 2H), 2.94 (t, 2H), 2.06 (m, 2H) |
| 2-21 | Cl | SEt | CH$_2$ | CH$_2$ | bond | CH$_2$ | |
| 2-22 | Cl | SOEt | CH$_2$ | CH$_2$ | bond | CH$_2$ | |
| 2-23 | Cl | SO$_2$Et | CH$_2$ | CH$_2$ | bond | CH$_2$ | |

TABLE 3

Inventive compounds of the general formula (I) in which Q is $Q^3$, in which $R^4$ is methyl, and $Z^4$ is a direct bond

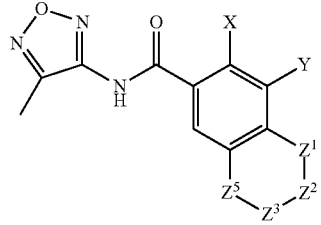

| No. | X | Y | $Z^1$ | $Z^2$ | $Z^3$ | $Z^5$ | Physical data ($^1$H NMR, DMSO-$d_6$, 400 MHz) |
|---|---|---|---|---|---|---|---|
| 3-1 | Me | Cl | CH$_2$ | CH$_2$ | bond | CH$_2$ | |
| 3-2 | Me | Cl | CH$_2$ | CH$_2$ | bond | CH$_2$ | |
| 3-3 | Me | Cl | CH$_2$ | CH$_2$ | bond | CH$_2$ | |
| 3-4 | Et | Cl | CH$_2$ | CH$_2$ | bond | CH$_2$ | |
| 3-5 | Et | Cl | CH$_2$ | CH$_2$ | bond | CH$_2$ | |
| 3-6 | nPr | Cl | CH$_2$ | CH$_2$ | bond | CH$_2$ | |
| 3-7 | cPr | Cl | CH$_2$ | CH$_2$ | bond | CH$_2$ | |
| 3-8 | Me | SMe | CH$_2$ | CH$_2$ | bond | CH$_2$ | |
| 3-9 | Me | SOMe | CH$_2$ | CH$_2$ | bond | CH$_2$ | |
| 3-10 | Me | SO$_2$Me | CH$_2$ | CH$_2$ | bond | CH$_2$ | |
| 3-11 | Me | SEt | CH$_2$ | CH$_2$ | bond | CH$_2$ | |
| 3-12 | Me | SOEt | CH$_2$ | CH$_2$ | bond | CH$_2$ | |
| 3-13 | Me | SO$_2$Et | CH$_2$ | CH$_2$ | bond | CH$_2$ | |
| 3-14 | Cl | Cl | CH$_2$ | CH$_2$ | bond | CH$_2$ | |
| 3-15 | Cl | Cl | CH$_2$ | CH$_2$ | bond | CH$_2$ | |
| 3-16 | Cl | Cl | CH$_2$ | CH$_2$ | bond | CH$_2$ | |
| 3-17 | Cl | Br | CH$_2$ | CH$_2$ | bond | CH$_2$ | |
| 3-18 | Cl | SMe | CH$_2$ | CH$_2$ | bond | CH$_2$ | 11.34 (bs, 1H), 7.49 (s1H), 3.10 (t, 2H), 2.96 (t, 2H), 2.40 (s, 3H), 2.38 (t, 3H), 2.08 (m, 2H) |
| 3-19 | Cl | SOMe | CH$_2$ | CH$_2$ | bond | CH$_2$ | 11.41 (bs, 1H), 7.70 (s1H), 3.52-3.22 (m, 2H), 2.93 (s, 3H), 2.88 (t, 2H), 2.38 (s, 3H), 2.10 (m, 2H) |
| 3-20 | Cl | SO$_2$Me | CH$_2$ | CH$_2$ | bond | CH$_2$ | 11.50 (bs, 1H), 7.84 (s1H), 3.39 (s, 3H), 3.36 (t, 2H), 2.94 (t, 2H), 2.40 (s, 3H), 2.06 (m, 2H) |
| 3-21 | Cl | SEt | CH$_2$ | CH$_2$ | bond | CH$_2$ | |
| 3-22 | Cl | SOEt | CH$_2$ | CH$_2$ | bond | CH$_2$ | |
| 3-23 | Cl | SO$_2$Et | CH$_2$ | CH$_2$ | bond | CH$_2$ | |

TABLE 4

Inventive compounds of the general formula (I) in which Q is $Q^4$, in which $R^5$ is methyl, and $Z^4$ is a direct bond

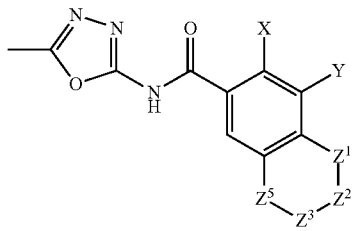

| No. | X | Y | $Z^1$ | $Z^2$ | $Z^3$ | $Z^5$ | Physical data ($^1$H NMR, DMSO-$d_6$, 400 MHz) |
|---|---|---|---|---|---|---|---|
| 4-1 | Me | Cl | CH$_2$ | CH$_2$ | bond | CH$_2$ | |
| 4-2 | Me | Cl | CH$_2$ | CH$_2$ | bond | CH$_2$ | |
| 4-3 | Me | Cl | CH$_2$ | CH$_2$ | bond | CH$_2$ | |
| 4-4 | Et | Cl | CH$_2$ | CH$_2$ | bond | CH$_2$ | |
| 4-5 | Et | Cl | CH$_2$ | CH$_2$ | bond | CH$_2$ | |
| 4-6 | nPr | Cl | CH$_2$ | CH$_2$ | bond | CH$_2$ | |
| 4-7 | cPr | Cl | CH$_2$ | CH$_2$ | bond | CH$_2$ | |
| 4-8 | Me | SMe | CH$_2$ | CH$_2$ | bond | CH$_2$ | |
| 4-9 | Me | SOMe | CH$_2$ | CH$_2$ | bond | CH$_2$ | |
| 4-10 | Me | SO$_2$Me | CH$_2$ | CH$_2$ | bond | CH$_2$ | |
| 4-11 | Me | SEt | CH$_2$ | CH$_2$ | bond | CH$_2$ | |
| 4-12 | Me | SOEt | CH$_2$ | CH$_2$ | bond | CH$_2$ | |
| 4-13 | Me | SO$_2$Et | CH$_2$ | CH$_2$ | bond | CH$_2$ | |
| 4-14 | Cl | Cl | CH$_2$ | CH$_2$ | bond | CH$_2$ | |
| 4-15 | Cl | Cl | CH$_2$ | CH$_2$ | bond | CH$_2$ | |
| 4-16 | Cl | Cl | CH$_2$ | CH$_2$ | bond | CH$_2$ | |
| 4-17 | Cl | Br | CH$_2$ | CH$_2$ | bond | CH$_2$ | |
| 4-18 | Cl | SMe | CH$_2$ | CH$_2$ | bond | CH$_2$ | 12.06 (bs, 1H), 7.42 (s1H), 3.09 (t, 2H), 2.93 (t, 2H), 2.47 (s, 3H), 2.39 (s, 3H), 2.07 (m, 2H) |
| 4-19 | Cl | SOMe | CH$_2$ | CH$_2$ | bond | CH$_2$ | |
| 4-20 | Cl | SO$_2$Me | CH$_2$ | CH$_2$ | bond | CH$_2$ | |
| 4-21 | Cl | SEt | CH$_2$ | CH$_2$ | bond | CH$_2$ | |
| 4-22 | Cl | SOEt | CH$_2$ | CH$_2$ | bond | CH$_2$ | |
| 4-23 | Cl | SO$_2$Et | CH$_2$ | CH$_2$ | bond | CH$_2$ | |

B. Formulation Examples a) A dusting product is obtained by mixing 10 parts by weight of a compound of the formula (I) and/or salts thereof and 90 parts by weight of talc as an inert substance and comminuting the mixture in a hammer mill.

b) A readily water-dispersible, wettable powder is obtained by mixing 25 parts by weight of a compound of the formula (I) and/or salts thereof, 64 parts by weight of kaolin-containing quartz as an inert substance, 10 parts by weight of potassium lignosulfonate and 1 part by weight of sodium oleoylmethyltaurate as a wetting agent and dispersant, and grinding the mixture in a pinned-disk mill.

c) A readily water-dispersible dispersion concentrate is obtained by mixing parts by weight of a compound of the formula (I) and/or salts thereof with 6 parts by weight of alkylphenol polyglycol ether (®Triton X 207), 3 parts by weight of isotridecanol polyglycol ether (8 EO) and 71 parts by weight of paraffinic mineral oil (boiling range for example about 255 to above 277 C), and grinding the mixture in a friction ball mill to a fineness of below 5 microns.

d) An emulsifiable concentrate is obtained from 15 parts by weight of a compound of the formula (I) and/or salts thereof, 75 parts by weight of cyclohexanone as a solvent and 10 parts by weight of ethoxylated nonylphenol as an emulsifier.

e) Water-dispersible granules are obtained by mixing 75 parts by weight of a compound of the formula (I) and/or salts thereof, 10 parts by weight of calcium lignosulfonate,
5 parts by weight of sodium lauryl sulfate,
3 parts by weight of polyvinyl alcohol and
7 parts by weight of kaolin,
grinding the mixture in a pinned-disk mill, and granulating the powder in a fluidized bed by spray application of water as a granulating liquid.

f) Water-dispersible granules are also obtained by homogenizing and precomminuting, in a colloid mill,
25 parts by weight of a compound of the formula (I) and/or salts thereof,
5 parts by weight of sodium 2,2'-dinaphthylmethane-6,6'-disulfonate
2 parts by weight of sodium oleoylmethyltaurate,
1 part by weight of polyvinyl alcohol
17 parts by weight of calcium carbonate and
50 parts by weight of water,
then grinding the mixture in a bead mill and atomizing and drying the resulting suspension in a spray tower by means of a one-phase nozzle.

C. Biological Examples

1. Pre-emergence Herbicidal Action Against Harmful Plants
Seeds of monocotyledonous and dicotyledonous weed plants and crop plants are laid out in wood-fiber pots in sandy loam and covered with soil. The compounds of the invention, formulated in the form of wettable powders (WP) or as emulsion concentrates (EC), are then applied to the surface of the covering soil in the form of an aqueous suspension or emulsion at a water application rate equating to 600 to 800 l/ha, with addition of 0.2% wetting agent. After the treatment, the pots are placed in a greenhouse and kept under good growth conditions for the trial plants. The damage to the test plants is scored visually after a test period of 3 weeks by comparison with untreated controls (herbicidal activity in percent (%): 100% activity=the plants have died, 0% activity=like control plants). For example, compounds no. 1-20, 1-23, 1-25, 1-26, 1-27, 1-52, 1-69, 1-75, 1-77 and 1-78 at an application rate of 320 g/ha each have at least 80% efficacy against *Abutilon theophrasti, Amaranthus retroflexus, Matricaria inodora, Pharbitis purpureum, Polygonum convolvulus, Setaria viridis, Stellaria media, Veronica persica* and *Viola* tricolor.

2. Post-emergence Herbicidal Action Against Harmful Plants

Seeds of monocotyledonous and dicotyledonous weed and crop plants are laid out in sandy loam in wood-fiber pots, covered with soil and cultivated in a greenhouse under good growth conditions. 2 to 3 weeks after sowing, the test plants are treated at the one-leaf stage. The compounds of the invention, formulated in the form of wettable powders (WP) or as emulsion concentrates (EC), are then sprayed onto the green parts of the plants in the form of an aqueous suspension or emulsion at a water application rate equating to 600 to 800 l/ha, with addition of 0.2% wetting agent. After the test plants have been left to stand in the greenhouse under optimal growth conditions for about 3 weeks, the action of the preparations is assessed visually in comparison to untreated controls (herbicidal action in percent (%): 100% activity=the plants have died, 0% activity=like control plants). For example, compounds no. 1-18, 1-19, 1-20, 1-21, 1-23, 1-25, 1-26, 1-27, 1-30, 1-32, 1-51, 1-52, 1-53, 1-63, 1-65, 1-69, 1-70, 1-75, 1-76, 1-77, 1-78, 1-79, 1-80, 1-84, 2-18, 2-20 and 4-18 at an application rate of 80 g/ha each have 100% efficacy against *Stellaria media, Veronica persica* and *Viola* tricolor.

The invention claimed is:
1. A bicyclic arylcarboxamide of the formula (I) or salt thereof

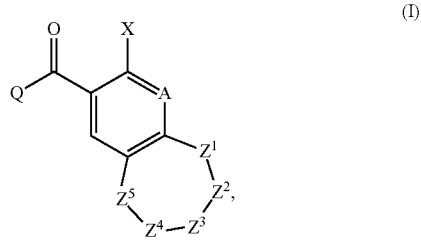

(I)

in which
A is N or CY,
X is nitro, halogen, cyano, formyl, thiocyanato, $(C_1-C_6)$-alkyl, halo-$(C_1-C_6)$-alkyl, $(C_2-C_6)$-alkenyl, halo-$(C_2-C_6)$-alkenyl, $(C_2-C_6)$-alkynyl, halo-$(C_3-C_6)$-alkynyl, $(C_3-C_6)$-cycloalkyl, halo-$(C_3-C_6)$-cycloalkyl, $(C_3-C_6)$-cycloalkyl-$(C_1-C_6)$-alkyl, halo-$(C_3-C_6)$-cycloalkyl-$(C_1-C_6)$-alkyl, $COR^1$, $COOR^1$, $OCOOR^1$, $NR^1COOR^1$, $C(O)N(R^1)_2$, $NR^1C(O)N(R^1)_2$, $OC(O)N(R^1)_2$, $C(O)NR^1OR^1$, $OR^1$, $OCOR^1$, $OSO_2R^2$, $S(O)_nR^2$, $SO_2R^1$, $SO_2N(R^1)_2$, $NR^1SO_2R^2$, $NR^1COR^1$, $(C_1-C_6)$-alkyl-S$(O)_nR^2$, $(C_1-C_6)$-alkyl-OR$^1$, $(C_1-C_6)$-alkyl-OCOR$^1$, $(C_1-C_6)$-alkyl-OSO$_2R^2$, $(C_1-C_6)$-alkyl-CO$_2R^1$, $(C_1-C_6)$-alkyl-SO$_2$OR$^1$, $(C_1-C_6)$-alkyl-CON(R$^1$)$_2$, $(C_1-C_6)$-alkyl-SO$_2$N(R$^1$)$_2$, $(C_1-C_6)$-alkyl-NR$^1$COR$^1$, $(C_1-C_6)$-alkyl-NR$^1$SO$_2R^2$, $NR_1R_2$, $P(O)(OR^{11})_2$, $CH_2P(O)(OR^{11})_2$, $(C_1-C_6)$-alkylheteroaryl, $(C_1-C_6)$-alkylheterocyclyl, where the latter two radicals are each substituted by s radicals from the group consisting of halogen, $(C_1-C_6)$-alkyl, halo-$(C_1-C_6)$-alkyl, $S(O)_n$-$(C_1-C_6)$-alkyl, $(C_1-C_6)$-alkoxy and halo-$(C_1-C_6)$-alkoxy, and where heterocyclyl bears n oxo groups, Y is hydrogen, nitro, halogen, cyano, thiocyanato, $(C_1-C_6)$-alkyl, halo-$(C_1-C_6)$-alkyl, $(C_2-C_6)$-alkenyl, halo-$(C_2-C_6)$-alkenyl, $(C_2-C_6)$-alkynyl, halo-$(C_2-C_6)$-alkynyl, $(C_3-C_6)$-cycloalkyl, $(C_3-C_6)$-cycloalkenyl, halo-$(C_3-C_6)$-cycloalkyl, $(C_3-C_6)$-cycloalkyl-$(C_1-C_6)$-alkyl, halo-$(C_3-C_6)$-cycloalkyl-$(C_1-C_6)$-alkyl, $COR^1$, $COOR^1$, $OCOOR^1$, $NR^1COOR^1$, $C(O)N(R^1)_2$, $NR^1C(O)N(R^1)_2$, $OC(O)N(R^1)_2$, $C(O)(NOR^1)R^1$, $C(NOR^1)R^1$, $NR^1SO_2R^2$, $N=S(O)R^2R^2$, $NR^1COR^1$, $OR^1$, $OSO_2R^2$, $S(O)_nR^2$, $S(O)(NR_2)R_2$, $SO2OR1$, $SO_2N(R^1)_2$, $(C_1-C_6)$-alkyl-S(O)$_nR^2$, $(C_1-C_6)$-alkyl-OR$^1$, $(C_1-C_6)$-alkyl-OCOR$^1$, $(C_1-C_6)$-alkyl-OSO2R$^2$, $(C_1-C_6)$-alkyl-CO$_2R^1$, $(C_1-C_6)$-alkyl-CN, $(C_1-C_6)$-alkyl-SO$_2$OR$^1$, $(C_1-C_6)$-alkyl-CON(R$^1$)$_2$, $(C_1-C_6)$-alkyl-SO$_2$N(R$^1$)$_2$, $(C_1-C_6)$-alkyl-NR$^1$COR$^1$, $(C_1-C_6)$-alkyl-NR$^1$SO$_2R^2$, $N(R^1)_2$, $P(O)(OR^{11})_2$, $CH_2P(O)(OR^{11})_2$, $(C_1-C_6)$-alkylphenyl, $(C_1-C_6)$-alkylheteroaryl, $(C_1-C_6)$-alkylheterocyclyl, phenyl, heteroaryl or heterocyclyl, where the latter six radicals are each substituted by s radicals from the group consisting of halogen, nitro, cyano, $(C_1-C_6)$-alkyl, halo-$(C_1-C_6)$-alkyl, $(C_3-C_6)$-cycloalkyl, $S(O)_n$—$(C_1-C_6)$-alkyl, $(C_1-C_6)$-alkoxy, halo-$(C_1-C_6)$-alkoxy, $(C_1-C_6)$-alkoxy-$(C_1-C_4)$-alkyl and cyanomethyl, and where heterocyclyl bears n oxo groups, $R^1$ is hydrogen, $(C_1-C_6)$-alkyl, $(C_1-C_6)$-haloalkyl, $(C_2-C_6)$-alkenyl, $(C_2-C_6)$-haloalkenyl, $(C_2-C_6)$-alkynyl, $(C_2-C_6)$-haloalkynyl, $(C_3-C_6)$-cycloalkyl, $(C_3-C_6)$-cycloalkenyl, $(C_3-C_6)$-halocycloalkyl, $(C_1-C_6)$-alkyl-O—$(C_1-C_6)$-alkyl, $(C_3-C_6)$-cycloalkyl-$(C_1-C_6)$-alkyl, phenyl, phenyl-$(C_1-C_6)$-alkyl, heteroaryl, $(C_1-C_6)$-alkylheteroaryl, heterocyclyl, $(C_1-C_6)$-alkylheterocyclyl, $(C_1-C_6)$-alkyl-O-heteroaryl, $(C_1-C_6)$-alkyl-O-heterocyclyl, $(C_1-C_6)$-alkyl-NR$^{12}$-heteroaryl or $(C_1-C_6)$-alkyl-NR$^{12}$-heterocyclyl, where the latter 21 radicals are each substituted by s radicals from the group consisting of cyano, halogen, nitro, thiocyanato, $OR^{12}$, $S(O)_nR^{13}$, $N(R^{12})_2$, $NR^{12}OR^{12}$, $COR^{12}$, $OCOR^{12}$, $SCOR^{13}$, $NR^{12}COR^{12}$, $NR^{12}SO_2R^{13}$, $CO_2R^{12}$, $COSR^{12}$, $CON(R^{12})_2$, $(C1-C6)$-alkyl and $(C_1-C_4)$-alkoxy-$(C_2-C_6)$-alkoxycarbonyl, and where heterocyclyl bears n oxo groups, $R^2$ is $(C_1-C_6)$-alkyl, $(C_1-C_6)$-haloalkyl, $(C_2-C_6)$-alkenyl, $(C_2-C_6)$-haloalkenyl, $(C_2-C_6)$-alkynyl, $(C_2-C_6)$-haloalkynyl, $(C_3-C_6)$-cycloalkyl, $(C_3-C_6)$-cycloalkenyl, $(C_3-C_6)$-halocycloalkyl, $(C_1-C_6)$-alkyl-O—$(C_1-C_6)$-alkyl, $(C_3-C_6)$-cycloalkyl-$(C_1-C_6)$-alkyl, phenyl, phenyl-$(C_1-C_6)$-alkyl, heteroaryl, $(C_1-C_6)$-alkylheteroaryl, heterocyclyl, $(C_1-C_6)$-alkylheterocyclyl, $(C_1-C_6)$-alkyl-O-heteroaryl, $(C_1-C_6)$-alkyl-O-heterocyclyl, $(C_1-C_6)$-alkyl-NR$^3$-heteroaryl or $(C_1-C_6)$-alkyl-NR$^3$-heterocyclyl, where the latter 21 radicals are each substituted by s radicals from the group consisting of cyano, halogen, nitro, thiocyanato, $OR^{12}$, $S(O)_nR^{13}$, $N(R^{12})_2$, $NR^{12}OR^{13}$, $COR^{12}$, $OCOR^{12}$, $SCOR^{13}$, $NR^{12}COR^{12}$, $NR^{12}SO_2R^{13}$, $CO_2R^{12}$, $COSR^{13}$, $CON(R^{12})_2$ and $(C_1-C_4)$-alkoxy-$(C_2-C_6)$-alkoxycarbonyl, and where heterocyclyl bears n oxo groups, Q is a $Q^1$, $Q^2$, $Q^3$ or $Q^4$ radical,

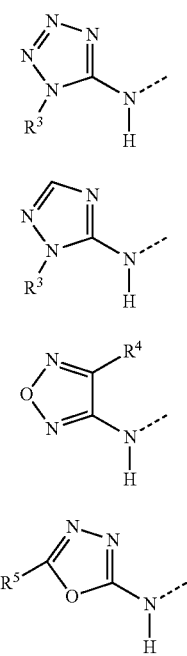

R³ is (C₁-C₈)-alkyl, (C₂-C₈)-alkenyl, (C₂-C₈)-alkynyl, where these radicals are each substituted by s radicals from the group consisting of halogen, cyano, hydroxyl, nitro, SiR$^{11}_3$, PO(OR$^{11}$)$_2$, S(O)$_n$—(C₁-C₆)-alkyl, (C₁-C₆)-alkoxy, halo-(C₁-C₆)-alkoxy, COR$^{3a}$, COOR$^{3a}$, OCOR$^{3a}$, NR$^{3a}$COR$^{3a}$, NR$^{3a}$SO$_2$R$^{3b}$, (C₃-C₆)-cycloalkyl, heteroaryl, heterocyclyl or phenyl, where the latter 4 radicals are each substituted by s radicals from the group consisting of methyl, ethyl, methoxy, trifluoromethyl, cyano and halogen, and where heterocyclyl bears n oxo groups, or R³ is phenyl substituted by s radicals from the group consisting of halogen, nitro, cyano, (C₁-C₆)-alkyl, halo-(C₁-C₆)-alkyl, (C₃-C₆)-cycloalkyl, S(O)$_n$—(C₁-C₆)-alkyl, (C₁-C₆)-alkoxy, halo-(C₁-C₆)-alkoxy and (C₁-C₆)-alkoxy-(C₁-C₄)-alkyl, R$^{3a}$ is hydrogen, (C₁-C₆)-alkyl, (C₂-C₆)-alkenyl, (C₂-C₆)-alkynyl, (C₃-C₆)-cycloalkyl, (C₃-C₆)-cycloalkyl-(C₁-C₆)-alkyl or phenyl, R$^{3b}$ is (C₁-C₆)-alkyl, (C₂-C₆)-alkenyl or (C₂-C₆)-alkynyl, (C₃-C₆)-cycloalkyl, (C₃-C₆)-cycloalkyl-(C₁-C₆)-alkyl or phenyl, R⁴ is hydrogen, (C₁-C₆)-alkyl, (C₃-C₇)-cycloalkyl, halo-(C₁-C₆)-alkyl, (C₁-C₆)-alkoxy, halo-(C₁-C₆)-alkoxy, (C₂-C₆)-alkenyl, (C₂-C₆)-alkenyloxy, (C₂-C₆)-haloalkenyl, (C₂-C₆)-alkynyl, (C₂-C₆)-alkynyloxy, (C₂-C₆)-haloalkynyl, (C₁-C₆)-alkoxy-(C₁-C₆)-alkyl, cyano, nitro, methylsulfenyl, methylsulfinyl, methylsulfonyl, acetylamino, benzoylamino, methoxycarbonyl, ethoxycarbonyl, methoxycarbonylmethyl, ethoxycarbonylmethyl, benzoyl, methylcarbonyl, piperidinylcarbonyl, trifluoromethylcarbonyl, halogen, amino, aminocarbonyl, methylaminocarbonyl, dimethylaminocarbonyl, methoxymethyl, or heteroaryl, heterocyclyl or phenyl, each substituted by s radicals from the group consisting of methyl, ethyl, methoxy, trifluoromethyl and halogen, R⁵ is hydrogen, (C₁-C₆)-alkyl, (C₁-C₆)-alkoxy-(C₁-C₆)-alkyl, CH₂R$^{5a}$, (C₃-C₇)-cycloalkyl, halo-(C₁-C₆)-alkyl, (C₂-C₆)-alkenyl, halo-(C₂-C₆)-alkenyl, (C₂-C₆)-alkynyl, halo-(C₂-C₆)-alkynyl, (C₁-C₆)-alkoxy, methylamino, methoxycarbonyl, ethoxycarbonyl, methoxycarbonylmethyl, ethoxycarbonylmethyl, methylcarbonyl, trifluoromethylcarbonyl, dimethylamino, acetylamino, methylsulfenyl, methylsulfinyl, methylsulfonyl, or heteroaryl, heterocyclyl, benzyl or phenyl, each substituted by s radicals from the group consisting of halogen, nitro, cyano, (C₁-C₆)-alkyl, halo-(C₁-C₆)-alkyl, (C₃-C₆)-cycloalkyl, S(O)$_n$—(C₁-C₆)-alkyl, (C₁-C₆)-alkoxy, halo-(C₁-C₆)-alkoxy and (C₁-C₆)-alkoxy-(C₁-C₄)-alkyl, R$^{5a}$ is acetoxy, acetamido, N-methylacetamido, benzoyloxy, benzamido, N-methylbenzamido, methoxycarbonyl, ethoxycarbonyl, benzoyl, methylcarbonyl, piperidinylcarbonyl, morpholinylcarbonyl, trifluoromethylcarbonyl, aminocarbonyl, methylaminocarbonyl, dimethylaminocarbonyl, (C₁-C₆)-alkoxy or (C₃-C₆)-cycloalkyl, or heteroaryl or heterocyclyl, each substituted by s radicals from the group consisting of methyl, ethyl, methoxy, trifluoromethyl and halogen, Z¹ is O, S(O)$_n$, CR⁶R⁶' or C=W, Z² is O, NR¹, CR⁷R⁷' or C=W, Z³ is a bond, O, CR⁸R⁸' or C=W, Z⁴ is a bond, O, CR⁹R⁹' or C=W, Z⁵ is O or CR¹⁰R¹⁰', with the proviso that at least one of these Z¹ to Z⁵ groups is a substituted carbon atom, and that two of these Z¹ to Z⁵ groups that are directly adjacent are not both oxygen, R⁶ and R⁶' are each independently hydrogen, halogen, cyano, hydroxyl, (C₁-C₄)-alkyl, (C₁-C₄)-haloalkyl, (C₁-C₄)-alkoxy, or R⁶ and R⁶' form a (C₂-C₅)-alkylene group in which n carbon atoms may be by oxygen, R⁷ and R⁷' are each independently hydrogen, halogen, cyano, hydroxyl, (C₁-C₄)-alkyl, (C₁-C₄)-haloalkyl, (C₁-C₄)-alkoxy, or R⁷ and R⁷' form a (C₂-C₅)-alkylene group in which n carbon atoms may be by oxygen, R⁸ and R⁸' are each independently hydrogen, halogen, cyano, hydroxyl, (C₁-C₄)-alkyl, (C₁-C₄)-haloalkyl, (C₁-C₄)-alkoxy, or R⁸ and R⁸' form a (C₂-C₅)-alkylene group in which n carbon atoms may be by oxygen, R⁹ and R⁹' are each independently hydrogen, halogen, cyano, hydroxyl, (C₁-C₄)-alkyl, (C₁-C₄)-haloalkyl, (C₁-C₄)-alkoxy, or R⁹ and R⁹' form a (C₂-C₅)-alkylene group in which n carbon atoms may be by oxygen, R¹⁰ and R¹⁰' are each independently hydrogen, halogen, cyano, hydroxyl, (C₁-C₄)-alkyl, (C₁-C₄)-haloalkyl, (C₁-C₄)-alkoxy, or R¹⁰ and R¹⁰' form a (C₂-C₅)-alkylene group in which n carbon atoms may be by oxygen, W is oxygen, NOR¹, NNR¹R¹ or CR¹R¹, R¹¹ is (C₁-C₄)-alkyl, R¹² is hydrogen, (C₁-C₆)-alkyl, (C₂-C₆)-alkenyl, (C₂-C₆)-alkynyl, (C₃-C₆)-cycloalkyl, (C₃-C₆)-cycloalkyl-(C₁-C₆)-alkyl or phenyl, R¹³ is (C₁-C₆)-alkyl, (C₂-C₆)-alkenyl, (C₂-C₆)-alkynyl, (C₃-C₆)-cycloalkyl, (C₃-C₆)-cycloalkyl-(C₁-C₆)-alkyl or phenyl, n is 0, 1 or 2, s is 0, 1, 2, 3, 4 or 5.

2. A bicyclic arylcarboxamide, of the formula (I) or salt thereof

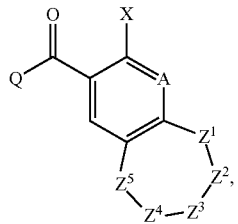

(I)

in which

A is N or CY,

X is nitro, halogen, cyano, thiocyanato, $(C_1-C_6)$-alkyl, halo-$(C_1-C_6)$-alkyl, $(C_2-C_6)$-alkenyl, halo-$(C_2-C_6)$-alkenyl, $(C_2-C_6)$-alkynyl, halo-$(C_3-C_6)$-alkynyl, $(C_3-C_6)$-cycloalkyl, halo-$(C_3-C_6)$-cycloalkyl, $(C_1-C_6)$-alkyl-O—$(C_1-C_6)$-alkyl, $(C_3-C_6)$-cycloalkyl-$(C_1-C_6)$-alkyl, halo-$(C_3-C_6)$-cycloalkyl-$(C_1-C_6)$-alkyl, $COR^1$, $OR^1$, $OCOR^1$, $OSO_2R^2$, $S(O)_nR^2$, $SO_2OR^1$, $SO_2N(R^1)_2$, $NR^1SO_2R^2$, $NR^1COR^1$, $(C_1-C_6)$-alkyl-$S(O)_nR^2$, $(C_1-C_6)$-alkyl-$OR^1$, $(C_1-C_6)$-alkyl-$OCOR^1$, $(C_1-C_6)$-alkyl-$OSO_2R^2$, $(C_1-C_6)$-alkyl-$CO_2R^1$, $(C_1-C_6)$-alkyl-$SO_2OR^1$, $(C_1-C_6)$-alkyl-$CON(R^1)_2$, $(C_1-C_6)$-alkyl-$SO_2N(R^1)_2$, $(C_1-C_6)$-alkyl-$NR^1COR^1$ or $(C_1-C_6)$-alkyl-$NR^1SO_2R^2$, $(C_1-C_6)$-alkylheteroaryl, $(C_1-C_6)$-alkylheterocyclyl, where the latter two radicals may each be substituted by s radicals from the group consisting of halogen, $(C_1-C_6)$-alkyl, halo-$(C_1-C_6)$-alkyl, $S(O)_n$—$(C_1-C_6)$-alkyl, $(C_1-C_6)$-alkoxy and halo-$(C_1-C_6)$-alkoxy, and where heterocyclyl bears n oxo groups, Y is hydrogen, nitro, halogen, cyano, thiocyanato, $(C_1-C_6)$-alkyl, halo-$(C_1-C_6)$-alkyl, $(C_2-C_6)$-alkenyl, halo-$(C_2-C_6)$-alkenyl, $(C_2-C_6)$-alkynyl, halo-$(C_3-C_6)$-alkynyl, $(C_3-C_6)$-cycloalkyl, $(C_3-C_6)$-cycloalkenyl, halo-$(C_3-C_6)$-cycloalkyl, $(C_3-C_6)$-cycloalkyl-$(C_1-C_6)$-alkyl, halo-$(C_3-C_6)$-cycloalkyl-$(C_1-C_6)$-alkyl, $COR^1$, $OR^1$, $COOR^1$, $OSO_2R^2$, $S(O)_nR^2$, $SO_2OR^1$, $SO_2N(R^1)_2$, $N(R^1)_2$, $NR^1SO_2R^2$, $NR^1COR^1$, $(C_1-C_6)$-alkyl-$S(O)_nR^2$, $(C_1-C_6)$-alkyl-$OR^1$, $(C_1-C_6)$-alkyl-$OCOR^1$, $(C_1-C_6)$-alkyl-$OSO_2R^2$, $(C_1-C_6)$-alkyl-$CO_2R^1$, $(C_1-C_6)$-alkyl-$SO_2OR^1$, $(C_1-C_6)$-alkyl-$CON(R^1)_2$, $(C_1-C_6)$-alkyl-$SO_2N(R^1)_2$, $(C_1-C_6)$-alkyl-$NR^1COR^1$, $(C_1-C_6)$-alkyl-$NR^1SO_2R^2$, $(C_1-C_6)$-alkylphenyl, $(C_1-C_6)$-alkylheteroaryl, $(C_1-C_6)$-alkylheterocyclyl, phenyl, heteroaryl or heterocyclyl, where the latter six radicals are each substituted by s radicals from the group consisting halogen, nitro, cyano, $(C_1-C_6)$-alkyl, halo-$(C_1-C_6)$-alkyl, $(C_3-C_6)$-cycloalkyl, $S(O)_n$—$(C_1-C_6)$-alkyl, $(C_1-C_6)$-alkoxy, halo-$(C_1-C_6)$-alkoxy, $(C_1-C_6)$-alkoxy-$(C_1-C_4)$-alkyl and cyanomethyl, and where heterocyclyl bears n oxo groups, $R^1$ is hydrogen, $(C_1-C_6)$-alkyl, $(C_2-C_6)$-alkenyl, $(C_2-C_6)$-alkynyl, $(C_3-C_6)$-cycloalkyl, $(C_3-C_6)$-cycloalkyl-$(C_1-C_6)$-alkyl, $(C_1-C_6)$-alkyl-O—$(C_1-C_6)$-alkyl, phenyl, phenyl-$(C_1-C_6)$-alkyl, heteroaryl, $(C_1-C_6)$-alkylheteroaryl, heterocyclyl, $(C_1-C_6)$-alkylheterocyclyl, $(C_1-C_6)$-alkyl-O-heteroaryl, $(C_1-C_6)$-alkyl-O-heterocyclyl, $(C_1-C_6)$-alkyl-$NR^{12}$-heteroaryl or $(C_1-C_6)$-alkyl-$NR^{12}$-heterocyclyl, where the latter sixteen radicals are each substituted by s radicals from the group consisting of cyano, halogen, nitro, $OR^{12}$, $S(O)_nR^{13}$, $N(R^{12})_2$, $NR^{12}OR^{12}$, $COR^{12}$, $OCOR^{12}$, $NR^{12}COR^{12}$, $NR^{12}SO_2R^{13}$, $CO_2R^{12}$, $CON(R^{12})_2$ and $(C_1-C_4)$-alkoxy-$(C_2-C_6)$-alkoxycarbonyl, and where heterocyclyl bears n oxo groups, $R^2$ is $(C_1-C_6)$-alkyl, $(C_2-C_6)$-alkenyl, $(C_2-C_6)$-alkynyl, $(C_3-C_6)$-cycloalkyl, $(C_3-C_6)$-cycloalkyl-$(C_1-C_6)$-alkyl, $(C_1-C_6)$-alkyl-O—$(C_1-C_6)$-alkyl, phenyl, phenyl-$(C_1-C_6)$-alkyl, heteroaryl, $(C_1-C_6)$-alkylheteroaryl, heterocyclyl, $(C_1-C_6)$-alkylheterocyclyl, $(C_1-C_6)$-alkyl-O-heteroaryl, $(C_1-C_6)$-alkyl-O-heterocyclyl, $(C_1-C_6)$-alkyl-$NR^{12}$-heteroaryl or $(C_1-C_6)$-alkyl-$NR^{12}$-heterocyclyl, where these latter sixteen radicals are each substituted by s radicals from the group consisting of cyano, halogen, nitro, $OR^{12}$, $S(O)_nR^{13}$, $N(R^{12})_2$, $NR^{12}OR^{12}$, $NR^{12}SO_2R^{13}$, $COR^{12}$, $OCOR^{12}$, $NR^{12}COR^{12}$, $CO_2R^{12}$, $CON(R^{12})_2$ and $(C_1-C_4)$-alkoxy-$(C_2-C_6)$-alkoxycarbonyl, and where heterocyclyl bears n oxo groups, Q is a $Q^1$, $Q^2$, $Q^3$ or $Q^4$ radical,

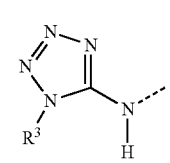

$Q^1$

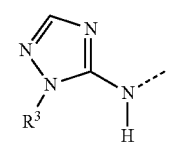

$Q^2$

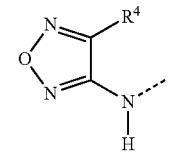

$Q^3$

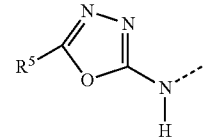

$Q^4$ $R^3$ is $(C_1-C_8)$-alkyl, $(C_2-C_8)$-alkenyl, $(C_2-C_8)$-alkynyl, where these radicals are each substituted by s radicals from the group consisting of halogen, cyano, nitro, $S(O)_n$—$(C_1-C_6)$-alkyl, $(C_1-C_6)$-alkoxy, halo-$(C_1-C_6)$-alkoxy, $(C_3-C_6)$-cycloalkyl, heteroaryl, heterocyclyl or phenyl, where the latter 4 radicals are each substituted by s radicals from the group consisting of methyl, ethyl, methoxy, trifluoromethyl, cyano and halogen, and where heterocyclyl bears n oxo groups, or $R^3$ is phenyl substituted in each case by s radicals from the group consisting of halogen, nitro, cyano, $(C_1-C_6)$-alkyl, halo-$(C_1-C_6)$-alkyl, $(C_3-C_6)$-cycloalkyl, $S(O)_n$—$(C_1-C_6)$-alkyl, $(C_1-C_6)$-alkoxy, halo-$(C_1-C_6)$-alkoxy and $(C_1-C_6)$-alkoxy-$(C_1-C_4)$-alkyl, $R^4$ is $(C_1-C_6)$-alkyl, $(C_3-C_7)$-cycloalkyl, halo-$(C_1-C_6)$-alkyl, $(C_1-C_6)$-alkoxy, halo-$(C_1-C_6)$-alkoxy, cyano, nitro, methylsulfenyl, methylsulfinyl, methylsulfonyl, $(C_1-C_4)$-alkylcarbonylamino, benzoylamino, methoxycarbonyl, ethoxycarbonyl, benzoyl, phenoxy, methylcarbonyl, piperidinylcarbonyl, trifluoromethylcarbonyl, halogen, amino, aminocarbonyl, methylaminocarbonyl, dimethylaminocarbonyl, methoxymethyl, 1,2,4-triazol-1-yl, pyrazol-1-yl, 2-thiophenyl, 2-pyridinyl, 3-pyridinyl, 4-pyridinyl, 1,2,4-oxadiazol-3-yl, benzoxazol-2-yl, 1-ethylbenzimidazol-2-yl, piperidin-1-yl, or phenyl substituted in each case by s radicals from the group consisting of methyl, ethyl, methoxy, trifluoromethyl and halogen, $R^5$ is hydrogen, $(C_1-C_6)$-alkyl, $(C_3-C_7)$-cycloalkyl, halo-$(C_1-C_6)$-alkyl, $(C_3-C_7)$-cycloalkylmethyl, methoxycarbonylmethyl, ethoxycarbonylmethyl, acetylmethyl, methoxymethyl, methoxyethyl, benzyl, pyrazin-2-yl, furan-2-yl, tetrahydrofuran-2-yl, morpholine or dimethylamino, or phenyl substituted by s radicals from the group consisting of methyl, methoxy, trifluoromethyl and halogen, $Z^1$ is O, $S(O)_n$, $CR^6R^{6'}$ or C=W,
$Z^2$ is O, NMe or $CH_2$,
$Z^3$ is a bond, O or $CH_2$,
$Z^4$ is a bond,
$Z^5$ is O or $CH_2$,
with the proviso that at least one of these $Z^1$ to $Z^5$ groups is a substituted carbon atom, and that two of these $Z^1$ to $Z^5$ groups that are directly adjacent are not both oxygen, $R^{10}$ and $R^{10'}$ are each independently hydrogen, halogen, cyano, hydroxyl, $(C_1-C_4)$-alkyl, $(C_1-C_4)$-haloalkyl, $(C_1-C_4)$-alkoxy,
or $R^{10}$ and $R^{10'}$ form a $(C_2-C_5)$-alkylene group in which n carbon atoms may be by oxygen,
W is oxygen, $NO(C_1-C_6)$-alkyl, $CH_2$, CHMe, $CMe_2$
$R^{12}$ is hydrogen or $(C_1-C_6)$-alkyl,
$R^{13}$ is $(C_1-C_6)$-alkyl,
n is 0, 1 or 2,
s is 0, 1, 2, 3, 4 or 5.

3. A bicyclic arylcarboxamide, of the formula (I) or salt thereof

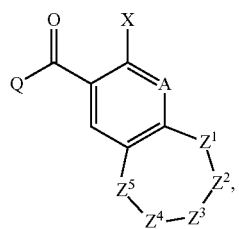
(I)

in which
A is N or CY,
X is nitro, halogen, cyano, $(C_1-C_6)$-alkyl, halo-$(C_1-C_6)$-alkyl, $(C_3-C_6)$-cycloalkyl, $OR^1$, $S(O)_nR^2$, $(C_1-C_6)$-alkyl-$S(O)_nR^2$, $(C_1-C_6)$-alkyl-$OR^1$, $(C_1-C_6)$-alkyl-$CON(R^1)_2$, $(C_1-C_6)$-alkyl-$SO_2N(R^1)_2$, $(C_1-C_6)$-alkyl-$NR^1COR^1$, $(C_1-C_6)$-alkyl-$NR^1SO_2R^2$, $(C_1-C_6)$-alkylheteroaryl, $(C_1-C_6)$-alkylheterocyclyl, where the latter two radicals are each substituted by s halogen, $(C_1-C_6)$-alkyl, halo-$(C_1-C_6)$-alkyl, $S(O)_n$—$(C_1-C_6)$-alkyl, $(C_1-C_6)$-alkoxy and halo-$(C_1-C_6)$-alkoxy radicals, and where heterocyclyl bears n oxo groups, Y is hydrogen, nitro, halogen, cyano, $(C_1-C_6)$-alkyl, $(C_1-C_6)$-haloalkyl, $OR^1$, $S(O)_nR^2$, $SO_2N(R^1)_2$, $N(R^1)_2$, $NR^1SO_2R^2$, $NR^1COR^1$, $(C_1-C_6)$-alkyl-$S(O)_nR^2$, $(C_1-C_6)$-alkyl-$OR^1$, $(C_1-C_6)$-alkyl-$CON(R^1)_2$, $(C_1-C_6)$-alkyl-$SO_2N(R^1)_2$, $(C_1-C_6)$-alkyl-$NR^1COR^1$, $(C_1-C_6)$-alkyl-$NR^1SO_2R^2$, $(C_1-C_6)$-alkylphenyl, $(C_1-C_6)$-alkylheteroaryl, $(C_1-C_6)$-alkylheterocyclyl, phenyl, heteroaryl or heterocyclyl, where the latter six radicals are each substituted by s radicals from the group consisting halogen, nitro, cyano, $(C_1-C_6)$-alkyl, halo-$(C_1-C_6)$-alkyl, $(C_3-C_6)$-cycloalkyl, $S(O)_n$—$(C_1-C_6)$-alkyl, $(C_1-C_6)$-alkoxy, halo-$(C_1-C_6)$-alkoxy, $(C_1-C_6)$-alkoxy-$(C_1-C_4)$-alkyl and cyanomethyl, and where heterocyclyl bears n oxo groups, $R^1$ is hydrogen, $(C_1-C_6)$-alkyl, $(C_2-C_6)$-alkenyl, $(C_2-C_6)$-alkynyl, $(C_3-C_6)$-cycloalkyl, $(C_3-C_6)$-cycloalkyl-$(C_1-C_6)$-alkyl, $(C_1-C_6)$-alkyl-O—$(C_1-C_6)$-alkyl, phenyl, phenyl-$(C_1-C_6)$-alkyl, heteroaryl, $(C_1-C_6)$-alkylheteroaryl, heterocyclyl, $(C_1-C_6)$-alkylheterocyclyl, $(C_1-C_6)$-alkyl-O-heteroaryl, $(C_1-C_6)$-alkyl-O-heterocyclyl, $(C_1-C_6)$-alkyl-$NR^{12}$-heteroaryl or $(C_1-C_6)$-alkyl-$NR^3$-heterocyclyl, where the latter sixteen radicals are each substituted by s radicals from the group consisting of cyano, halogen, nitro, $OR^{12}$, $S(O)_nR^{13}$, $N(R^{12})_2$, $NR^{12}OR^{12}$, $COR^{12}$, $OCOR^{12}$, $NR^{12}COR^{12}$, $NR^{12}SO_2R^{13}$, $CO_2R^{12}$, $CON(R^{12})_2$ and $(C_1-C_4)$-alkoxy-$(C_2-C_6)$-alkoxycarbonyl, and where heterocyclyl bears n oxo groups, $R^2$ is $(C_1-C_6)$-alkyl, $(C_3-C_6)$-cycloalkyl or $(C_3-C_6)$-cycloalkyl-$(C_1-C_6)$-alkyl, each substituted by s radicals from the group consisting of halogen and $OR^{12}$, Q is a $Q^1$, $Q^2$, $Q^3$ or $Q^4$ radical,

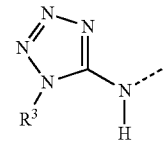
$Q^1$

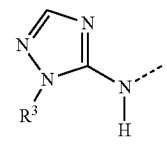
$Q^2$

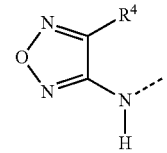
$Q^3$

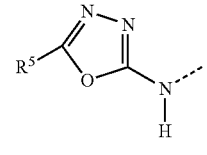
$Q^4$ $R^3$ is $(C_1-C_8)$-alkyl, $(C_2-C_8)$-alkenyl or $(C_2-C_8)$-alkynyl, each substituted by s radicals from the group consisting of halogen, cyano, nitro, $S(O)_n$—$(C_1-C_6)$-alkyl, $(C_1-C_6)$-alkoxy and halo-$(C_1-C_6)$-alkoxy, $R^4$ is $(C_1-C_6)$-alkyl, $(C_3-C_7)$-cycloalkyl, halo-$(C_1-C_6)$-alkyl, $(C_1-C_6)$-alkoxy, halo-$(C_1-C_6)$-alkoxy, cyano, nitro, methylsulfenyl, methylsulfinyl, methylsulfonyl, $(C_1-C_4)$-alkylcarbonylamino, benzoylamino, methoxycarbonyl, ethoxycarbonyl, benzoyl, phenoxy, methylcarbonyl, piperidinylcarbonyl, trifluoromethylcarbonyl, halogen, amino, aminocarbonyl, methylaminocarbonyl, dimethylaminocarbonyl, methoxymethyl, 1,2,4-triazole-1H, 1-pyrazole-1H, 2-thiophenyl, 2-pyridinyl, 3-pyridinyl, 4-pyridinyl, 1,2,4-oxadiazol-3-yl, benzoxazol-2-yl, 1-ethylbenzimidazol-2-yl, piperidin-1-yl, or phenyl substituted in each case by s radicals from the group consisting of methyl, ethyl, methoxy, trifluoromethyl and halogen, $R^5$ is hydrogen, $(C_1-C_6)$-alkyl, $(C_3-C_7)$-cycloalkyl, halo-$(C_1-C_6)$-alkyl, $(C_3-C_7)$-cycloalkylmethyl, methoxycarbonylmethyl, ethoxycarbonylmethyl, acetylmethyl, methoxymethyl, methoxyethyl, benzyl, pyrazin-$_2$-yl, furan-$_2$-yl, tetrahydrofuran-$_2$-yl, morpholine or dimethylamino, or phenyl substituted by s radicals from the group consisting of methyl, methoxy, trifluoromethyl and halogen, $Z^1$ is O, $SO_2$, $CR^6R^{6'}$ or C=W, $Z^2$ is O, NMe or $CH_2$, $Z^3$ is a bond, O or $CH_2$, $Z^4$ is a bond, $Z^5$ is O or $CH_2$, with the proviso that at least one of these $Z^1$ to $Z^5$ groups is a substituted carbon atom, and that two of these $Z^1$ to $Z^5$ groups that are directly adjacent are not both oxygen, $R^6$ and $R^{6'}$ are each independently hydrogen, fluorine, hydroxyl, $(C_1-C_4)$-alkyl, $(C_1-C_4)$-alkoxy, or $R^6$ and $R^{6'}$ form a $(C_2-C_5)$-alkylene group in which n carbon atoms may be by oxygen, W is oxygen or $NO(C_1-C_6)$-alkyl, $R^{12}$ is hydrogen or $(C_1-C_6)$-alkyl, $R^{13}$ is $(C_1-C_6)$-alkyl, n is 0, 1 or 2, s is 0, 1, 2, 3, 4 or 5.

4. A herbicidal composition, comprising a herbicidally active content of at least one bicyclic arylcarboxamide of the formula (I) or salt as claimed in claim 1.

5. The herbicidal composition as claimed in claim 4 in a mixture with one or more formulation auxiliaries.

6. The herbicidal composition as claimed in claim 4, comprising at least one further pesticidally active substance from the group consisting of insecticides, acaricides, herbicides, fungicides, safeners, and growth regulators.

7. The herbicidal composition as claimed in claim 6, comprising a safener.

8. The herbicidal composition as claimed in claim 7, comprising cyprosulfamide, cloquintocet-mexyl, mefenpyr-diethyl or isoxadifen-ethyl.

9. A method for controlling unwanted plants, comprising applying an effective amount of at least one bicyclic arylcarboxamide of the formula (I) or salt as claimed in claim 1 or a herbicidal composition thereof to the plants or to a site of unwanted vegetation.

10. A product comprising a bicyclic arylcarboxamide of the formula (I) or salt as claimed in claim 1 or herbicidal composition thereof for controlling unwanted plants.

11. A method as claimed in claim 9, comprising controlling unwanted plants in one or more crops of useful plants.

12. A method as claimed in claim 11, wherein the useful plants are transgenic useful plants.

13. A bicyclic arylcarboxamide or salt as claimed in claim 1, wherein A is N.

14. A bicyclic arylcarboxamide or salt as claimed in claim 1, wherein A is CY.

15. A bicyclic arylcarboxamide or salt as claimed in claim 1, wherein Q is $Q^1$.

16. A bicyclic arylcarboxamide or salt as claimed in claim 1, wherein Q is $Q^2$.

17. A bicyclic arylcarboxamide or salt as claimed in claim 1, wherein Q is $Q^3$.

18. A bicyclic arylcarboxamide or salt as claimed in claim 1, wherein Q is $Q^4$.

19. A bicyclic arylcarboxamide or salt as claimed in claim 1, wherein $Z^1$ is O.

20. A bicyclic arylcarboxamide or salt as claimed in claim 1, wherein $Z^1$ is $SO_2$.

* * * * *